(12) United States Patent
Shaw et al.

(10) Patent No.: US 8,003,610 B2
(45) Date of Patent: Aug. 23, 2011

(54) BRADYKININ $B_2$ RECEPTOR ANTAGONIST PEPTIDE FROM AMPHIBIAN SKIN

(75) Inventors: Chris Shaw, Comber (GB); David Hirst, Belfast (GB); Tianbao Chen, Belfast (GB); Martin O'Rourke, Carrickfergus (GB); Pingfan Rao, Fuzhou (CN)

(73) Assignee: Queen's University of Belfast, Belfast (GB)

( * ) Notice: Subject to any disclaimer, the term of this patent is extended or adjusted under 35 U.S.C. 154(b) by 1208 days.

(21) Appl. No.: 10/544,946

(22) PCT Filed: Feb. 6, 2004

(86) PCT No.: PCT/GB2004/000473
§ 371 (c)(1),
(2), (4) Date: Aug. 30, 2006

(87) PCT Pub. No.: WO2004/068928
PCT Pub. Date: Aug. 19, 2004

(65) Prior Publication Data
US 2008/0044463 A1    Feb. 21, 2008

(30) Foreign Application Priority Data

Feb. 6, 2003 (GB) .................................. 0302624.2
Oct. 3, 2003 (GB) .................................. 0323193.3

(51) Int. Cl.
*A61K 38/08* (2006.01)
*C07K 7/06* (2006.01)

(52) U.S. Cl. .............. 514/15; 514/2; 530/300; 530/328; 424/9.1; 424/450; 424/489

(58) Field of Classification Search ................ 514/2, 15; 530/300, 328; 424/9.1, 450, 489
See application file for complete search history.

(56) References Cited

FOREIGN PATENT DOCUMENTS
WO    WO 86/07263    12/1986

OTHER PUBLICATIONS

N. E. Rhaleb et al., "Structure-Activity Studies of Bradykinin and Related Peptides. B2-Receptor Antagonists", *Hypertension*, 17(1): 107-115 (1991).
Tianbao Chen et al., "Kinestatin: A Novel Bradykinin B2 Receptor Antagonist Peptide From the Skin Secretion of the Chinese Toad, Bombina Maxima", *Regulatory Peptides*, 116(1-3): 147-154 (2003).
R. Lai et al., "A Novel Bradykinin-Related Peptide From Skin Secretions of Toad Bombina Maxima and Its Precursor Containing Six Identical Copies of the Final Product", *Biochemical and Biophysical Research Communications*, 286(2): 259-263 (2001).

*Primary Examiner* — Chih-Min Kam
(74) *Attorney, Agent, or Firm* — Drinker Biddle & Reath LLP

(57) ABSTRACT

A bradykinin B2-receptor antagonist peptide, kinestatin, isolated from toad (*Bombina maxima*) defensive skin secretion, and analogs thereof, is disclosed. The structure of kinestatin is pGlu-Leu/Ile-Pro-Gly-Leu/Ile-Gly-Pro-Leu/Ile-Arg-$NH_2$.
Also disclosed are kinestatin analogs, prodrugs including the peptides, fusion peptides and multimeric peptides including the peptide sequences, pharmaceutical compositions including kinestatin and analogs thereof, prodrugs, fusion and multimeric peptides thereof, nucleic acids encoding kinestatin and analogs thereof, and nucleic acids encoding the fusion and multimeric peptides. Kinestatin and analogs thereof (including the prodrugs and multimeric and/or fusion peptides) can be used to treat and/or prevent disorders associated with bradykinin, including cardiovascular disorders, inflammation, asthma, allergic rhinitis, pain, angiogenesis and the like.

31 Claims, 14 Drawing Sheets

```
                                                         M   R   L   W   F   C   L
   1 TAGTTCTCAG TGTCACTTCC AGCTCTGATC ATGAGACTGT GGTTCTGTCT
     S   F   F   I   V   L   C   L   E   H   F   P   G   T   L   A
  51 AAGTTTTTC ATCGTCCTGT GCCTGGAGCA TTTTCCAGGA ACCCTGGCAG
     D   E   R   N   N   R   D   Y   T   I   R   T   R   L   H   G   H
 101 ATGAAAGGAA TAATCGTGAC TACACCATCA GAACCCGCTT ACATGGCCAT
     H   K   P   S   R   N   N   R   Y   A   I   K   T   S   I   H   G
 151 CATAAACCAA GCAGGAATAA CCGTTACGCC ATCAAAAACCA GCATACATGG
     H   H   I   P   R   N   V   P   E   S   E   E   K   T   E   Q
 201 CCATCATATA CCAAGGAATG TTCCAGAGAG TGAAGAAAAA ACTGAGCAGC
     L   L   R   D   L   P   K   I   N   R   K   G   P   R   P   P   G
 251 TCCTGAGGGA TTTGCCTAAG ATCAACCCGCA AAGGACCACG TCCACCGGGG
     F   S   P   F   R   G   K   F   H   S   Q   S   L   R   Q   I   P
 301 TTCTCCCCTT TTCGAGGAAA ATTCCATAGC CAGTCCCCTAC GACAAATTCC
     G   L   G   P   L   R   G   *
 351 TGGTTTAGGC CCTCTGCCTG GATAACGAAG CTCAGGGATA AGAATCTGCC
 401 CTATGTGTAT GCCATGTTCA CCATAGGCTA AAAAGTAGCG TCCCCTGCTA
 451 TAAATAAGCA TTGTTATGTC ACCTCTGTAA TACCAGCTCT GACTGACATG
 501 GTTTATTAAA CAGCAGATTT GTGCTCTCTA AAAAAAAAAA AAAAAAA
```

Fig. 3

BRADYKININ B₂ RECEPTOR ANTAGONIST PEPTIDE FROM AMPHIBIAN SKIN

This application is a 371 of PCT/GB04/00473, filed Feb. 6, 2004, which claims the priority of United Kingdom Patent Application No. 0302624.2, filed Feb. 6, 2003 and United Kingdom Patent Application No. 0323193.3, filed Oct. 3, 2003.

FIELD OF THE INVENTION

The present invention relates to peptides and uses thereof. In particular, it relates to bradykinin antagonist molecules.

INTRODUCTION

The formidable array of bioactive molecules, including peptides, present in amphibian skin, has been the subject of study for almost 40 years (Erspamer, V. (1984) Comp. Biochem. Physiol. 79C, 1-7.). The source of these molecular cocktails are the specialised poison or granular glands, that in response to stress or predator attack, secrete onto the skin surface (Erspamer, V., Melchiorri, P., Falconieri Erspamer, G. F., Montecucchi, P. P and De Castiglione R. (1985) Peptides 6Suppl. 3, 7-12). Since the pioneering studies on amphibian skin peptides by Vittorio Erspamer, several hundred peptides have been structurally-characterised and classified into families based upon structural similarities, e.g. bombesins, tachykinins and bradykinins (Lazarus, L. H. and Atilla, M. (1993) Prog. Neurobiol. 41, 473-507).

Bradykinins are found in the skin secretions of many anuran amphibians including representative species of the families, Ranidae, Hylidae and Bombinatoridae (Conlon, J. M. & Aronsson, U. (1997) Peptides 18, 361-365; Yasuhara, T., Ishikawa, O., Nakajima, T., Araki, K. and Tachibana, S. (1979) Chem. Pharm. Bull. (Tokyo) 27, 486-491; Anastasi, A., Bertaccini, G. and Erspamer, V. (1966) Br. J. Pharmacol. 27, 479-485; Yasuhara, T., Hira, M., Nakajima, T., Yanaihara, N. and Yanaihara, C. (1973) Chem. Pharm. Bull. (Tokyo) 21, 1388-139; Lai R., Liu H., Hui Lee W. and Zhang Y. (2001) Biochem. Biophys. Res. Commun. 286, 259-263).

The actions of bradykinin are diverse, including vasodilation with subsequent induced hypotension, increasing vascular permeability, induction of pain and contraction of a variety of smooth muscle types (Regoli, D., Rizzi, A. and Cab, G. (1997) Pharmacol. Res. 35, 513-515). However, the actions of some structural variants such as phyllokinin (bradykinyl-IYsulphate from *Phyllomedusa* sp.) are often more potent and prolonged, e.g. on vasodilation/hypotension induction (Anastasi, A., Bertaccini, G. and Erspamer, V. (1966) Br. J. Pharmacol. 27, 479-485).

In contrast to the strategy of supraphysiological delivery of bradykinin agonists evolved in amphibians, the haemotoxic snakes are quite different. These reptile venoms are a rich source of small peptides that potentiate the action of bradykinin on mammalian vascular smooth muscle by inhibiting angiotensin-converting enzyme (ACE) (Higuchi, S., Murayama, N., Saguchi, K., Ohi, H., Fujita, Y., Camargo, A. C. M., Ogawa, T., Deshimaru, M. and Ohno, M. (1999) Immunopharmacology 44, 129-135). The type peptides, from the venom of the Brazilian viper, Bothrops jararaca, were the lead compounds in ACE inhibitor drug development that are now the mainstay in the treatment of hypertension (Moser, M. (2002) J. Hypertension 20, S3-S10).

Being unaware of any previous studies directed at determining if amphibian skin analogues to reptile venom brady-kinin-potentiating peptides existed, we embarked on a systematic study designed to address this question.

SUMMARY OF THE INVENTION

Surprisingly, in their search for an amphibian bradykinin potentiating peptide, the present inventors have found a bradykinin receptor antagonist peptide in the skin secretion of the Chinese toad, *Bombina maxima*. This peptide, hereinafter referred to as kinestatin, represents an entirely novel structural class of amphibian skin peptide displaying a unique bradykinin inhibitory activity.

Accordingly, in a first aspect, the present invention provides an isolated peptide having bradykinin antagonist activity, wherein said peptide comprises the amino acid sequence:

$Xaa_1$-$Xaa_2$-$Xaa_3$-Gly-Leu-$Xaa_6$-Pro-$Xaa_8$-$Xaa_9$ (SEQ ID NO: 1) or a fragment thereof, or the amino acid sequence: $Xaa_9$-$Xaa_8$-Pro-$Xaa_6$-Leu-Gly-$Xaa_3$-$Xaa_2$-$Xaa_1$ (SEQ ID NO: 2), or a fragment thereof;

wherein $Xaa_1$, $Xaa_2$, $Xaa_3$, $Xaa_6$, $Xaa_8$ and $Xaa_9$ are each independently any amino acid.

Preferably $Xaa_1$ is pGlu. Preferably, $Xaa_8$ is Leu. Preferably $Xaa_9$ is Arg. Preferably, the C-terminal peptide is amidated.

In particularly preferred embodiments of the invention, the peptide of and for use in the methods of the invention comprises the amino acid sequence:

pGlu-Ile-Pro-Gly-Leu-Gly-Pro-Leu-Arg.$NH_2$ (SEQ ID NO: 3). In a further preferred embodiment, the peptide comprises the reverse peptide sequence of SEQ ID NO: 3 i.e. Arg-Leu-Pro-Gly-Leu-Gly-Pro-Ile-pGlu.$NH_2$ (SEQ ID NO: 4).

The peptide of the invention may be of any length, as long as it retains bradykinin inhibitory activity. Preferably, the peptide of and for use in the invention has bradykinin $B_2$ receptor antagonist activity. However, in preferred embodiments, the peptide is a nonapeptide. In a particularly preferred embodiment, the peptide is a nonapeptide having an amino acid sequence:

pGlu-Ile-Pro-Gly-Leu-Gly-Pro-Leu-Arg.$NH_2$ (SEQ ID NO: 3).

It should be understood that peptides according to the first aspect of the invention encompass peptides without post-translational modifications. For example, (for example, a peptide having the sequence corresponding to that of SEQ ID No: 3 in which the C-terminal is not amidated and the N-terminal glutamine has not been cyclised to form pyroglutamate) is encompassed by the invention. However, in preferred embodiments, peptides having such post-translational modifications is preferred.

A peptide is considered to have bradykinin antagonist activity if in a defined bradykinin receptor containing pharmacological preparation, the peptide can effectively inhibit the pharmacological activity of bradykinin. In preferred embodiments, the peptide can effectively inhibit the pharmacological activity of bradykinin selectively at bradykinin $B_2$ receptors.

As a second aspect, the invention further provides an isolated polynucleotide encoding a peptide according to the first aspect of the invention. In a preferred embodiment, the polynucleotide comprises the sequence:

CAAATTCCTGGTTTAGGCCCTCTGCGT. (SEQ ID NO: 5)

Although the polynucleotides of the invention are generally in isolated form, they may be integrated with other genetic molecules, such as a vector molecule. Accordingly, in a third aspect of the present invention, there is provided a vector molecule comprising the isolated polynucleotide of the second aspect of the invention.

Further provided by the invention in a fourth aspect is a method of antagonising bradykinin activity in a cell, tissue or organism, said method comprising administering a peptide according to the first aspect of the invention, a polynucleotide according to the second aspect of the invention or a vector according to the third aspect of the invention to said cell, tissue or organism.

According to a fifth aspect of the present invention, there is provided a method of constricting vascular smooth muscle, said method comprising administering a peptide according to the first aspect of the invention, a polynucleotide according to the second aspect of the invention or a vector according to the third aspect of the invention to said smooth muscle.

The surprising demonstration that kinestatins exhibit significant bradykinin antagonism activity enables the use of such peptides and the polynucleotides encoding said polypeptides in the treatment of diseases, for example diseases of the cardiovascular system, neurological diseases or degenerative diseases, such as Alzheimer's disease.

Thus, according to a sixth aspect of the invention, there is provided a method of treating a condition associated with bradykinin activity, said method comprising administering a therapeutically effective amount of a peptide according to the first aspect of the invention, a polynucleotide according to the second aspect of the invention or a vector according to the third aspect of the invention to a patient in need thereof.

The peptides of the invention have also been found to inhibit angiogenesis. Thus, in a further aspect of the invention, there is provided a method of inhibiting angiogenesis, said method comprising administering a therapeutically effective amount of a peptide according to the first aspect of the invention, a polynucleotide according to the second aspect of the invention or a vector according to the third aspect of the invention to a patient in need thereof.

The invention may thus be used to treat disorders meadiated by angiogenesis, such as autoimmune disorders, rheumatoid arthritis. Thus, in a further aspect of the invention, there is provided a method of treating a disorder mediated by angiogenesis, for example rheumatoid arthritis, said method comprising administering a therapeutically effective amount of a peptide according to the first aspect of the invention, a polynucleotide according to the second aspect of the invention or a vector according to the third aspect of the invention to a patient in need thereof.

In a further aspect, there is provided a pharmaceutical composition comprising a peptide according to the first aspect of the invention, a polynucleotide according to the second aspect of the invention or a vector according to the third aspect of the invention, and a pharmaceutically acceptable carrier or excipient.

Another aspect of the invention provides a peptide according to the first aspect of the invention, a polynucleotide according to the second aspect of the invention or a vector according to the third aspect of the invention for use in medicine, for example for use in the treatment of cardiovascular disease or for the treatment of autoimmune disease.

Further provided by the invention, is the use of a peptide according to the first aspect of the invention, a polynucleotide according to the second aspect of the invention or a vector according to the third aspect of the invention in the preparation of, a medicament for the treatment of cardiovascular disease or for the treatment of autoimmune disease.

Preferred features of each aspect of the invention are as for each of the other aspects mutatis mutandis.

DETAILED DESCRIPTION

As described above, the present inventors have discovered a novel class of bradykinin inhibitor, which they have termed kinestatins. In particular, the inventors have found that kinestatins, e.g. SEQ ID NO: 3, have potent vasodilatory activity.

Any suitable kinestatin may be used in the present invention. In preferred embodiments the kinestatin comprises the amino acid sequence SEQ ID NO: 3 or a biologically active analogue or fragment thereof.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects. As used herein, a "partial agonist" is a substance that provides a level of stimulation to its binding partner that is intermediate between that of a full or complete antagonist and an agonist defined by any accepted standard for agonist activity. It will be recognized that stimulation, and hence, inhibition is defined intrinsically for any substance or category of substances to be defined as agonists, antagonists, or partial agonists. As used herein, "intrinsic activity," or "efficacy," relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. See, Hoyer and Boddeke, (1993) *Trends Pharmacol Sci.* 14(7): 270. Where such contextually specific evaluations are relevant, and how they might be relevant in the context of the present invention, will be apparent to one of ordinary skill in the art.

Biological Activity

Biological activity may be assessed by any means known in the art or as described herein. In preferred embodiments an analogue or fragment is considered to be biologically active if it is capable of inhibiting bradykinin induced vasodilation and/or is capable of inhibiting angiogenesis. Preferably, an analogue or fragment is considered to be biologically active i.e. have kinestatin activity if it is capable of inhibiting bradykinin induced vasodilation and is capable of inhibiting angiogenesis.

In preferred embodiments of the invention, the analogues or fragments of the invention are devoid of direct smooth muscle effects i.e. devoid of vasoactive effects.

In particularly preferred embodiments, the ID50 of the kinestatin or analogue or fragment at arterial smooth muscle is less than the ID50 of HOE 140, preferably at least ×10, for example at least ×20, more preferably at least ×30, even more preferably at least ×40, most preferably at least ×50 times less than the ID50 of HOE 140 in a comparable preparation. In particularly preferred embodiments, the ID50 of the kinestatin or analogue or fragment at arterial smooth muscle is of the order of $1\times10^{-8}$M compared to the ED50 of bradykinin ($5\times10^{-6}$M i.e. 50-100 times more potent than HOE 140 at antagonising the bradykinin $B_2$ receptor.

The biological activity of the kinestatin peptides (including fragments, variants, derivatives, and analogs thereof), may be assayed by various methods. For example, in one embodiment where one is assaying for the ability to bind or compete with kinestatin (or bradykinin) for binding to the bradykinin $B_2$ receptor, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immuno-electrophoresis assays, and the like. Many means are known in the art for detecting binding in an immunoassay and are within the scope of the present invention.

Where a kinestatin ligand is identified, or the ability of a polypeptide fragment, variant or derivative described herein to multimerize is being evaluated, binding can be assayed, e.g., by means well-known in the art, such as, for example, reducing and non-reducing gel chromatography, protein affinity chromatography, and affinity blotting. See generally, Phizicky, E., et al., *Microbiol. Rev.* 59:94-123 (1995).

Anti-angiogenesis activity may be assayed using any standard assays, such as the Matrigel assay and the assays used in the Examples.

Fragments

A "fragment" of a kinestatin means a stretch of amino acid residues of at least 6 amino acids, typically at least 7 amino acids, preferably at least 8 amino acids of a polypeptide having amino acid sequence shown as SEQ ID NO: 3, which retains kinestatin biological activity, for example, the ability to selectively antagonise bradykinin at bradykinin $B_2$ receptors.

Kinestatin analogues of and for use in the invention means a polypeptide modified by varying the amino acid sequence of a kinestatin e.g. SEQ ID NO: 1 or SEQ ID NO: 3, e.g. by manipulation of the nucleic acid encoding the protein or by altering the protein itself. Such analogues of the natural kinestatin amino acid sequence may involve insertion, addition, deletion and/or substitution of one or more amino acids, while providing a peptide capable of dilating arterial smooth muscle.

Preferably such analogues involve the insertion, addition, deletion and/or substitution of 15 or fewer amino acids, more preferably of 10 or fewer, even more preferably of 5 or fewer, most preferably of 1 or 2 amino acids only.

Analogues of the invention include multimeric or fusion peptides including such kinestatin peptide, analogue or fragment sequences, and prodrugs including such sequences, derivatives of the peptides of the invention, including the peptide linked to a coupling partner, e. g. an effector molecule, a label, a drug, a toxin and/or a carrier or transport molecule. Techniques for coupling the peptides of the invention to both peptidyl and non-peptidyl coupling partners are well known in the. art.

Analogues of the invention include fusion peptides. For example, analogues may comprise peptides of the invention linked, for example, to antibodies that target the peptides to diseased tissue, for example, heart tissue or tumor tissue.

The kinestatin peptides described herein may be fused with the constant domain of immunoglobulins (IgA, IgE, IgG, IgM), or portions thereof (CH1, CH2, CH3, or any combination thereof) and portions thereof, resulting in chimeric polypeptides. These fusion proteins can facilitate purification and show an increased half-life in vivo. Such fusion proteins may be more efficient in binding and neutralizing other molecules than monomeric polypeptides or fragments thereof alone. See, e.g., Fountoulakis et al., J. Biochem., 270:3958-3964 (1995).

Fusion proteins of the invention also include kinestatin peptides fused with albumin, for example recombinant human serum albumin or fragments or variants thereof (see, e.g., U.S. Pat. No. 5,876,969, EP Patent 0 413 622, and U.S. Pat. No. 5,766,883).

Polynucleotides encoding such fusion proteins described herein are also encompassed by the invention.

Reverse Peptide Analogues

Analogues of and for use in the present invention further include reverse-or retro-analogues of natural peptides or their synthetic derivatives. See, for example, EP 0497 366, U.S. Pat. No. 5,519,115, and Merrifield et al., 1995, PNAS, 92:3449-53, the disclosures of which are herein incorporated by reference. As described in EP 0497 366, reverse peptides are produced by reversing the amino acid sequence of a naturally occurring or synthetic peptide. Such reverse-peptides retain the same general three-dimensional structure (e. g., alpha-helix) as the parent peptide except for the confirmation around internal protease-sensitive sites and the characteristics of the N- and C-termini. Reverse peptides are purported not only to retain the biological activity of the non-reversed "normal" peptide but may possess enhanced properties, including increased biological activity. (See Iwahori et al., 1997, Biol. Pharm. Bull. 20: 267-70). Analogues of and for use in the present invention may therefore comprise reverse peptides of natural and synthetic kinestatins.

In preferred embodiments, preferred reverse peptides include peptides having the generic formula:
Arg-Xaa-Pro-Xaa-Leu-Gly-Xaa-Xaa-Xaa (SEQ ID NO: 22; wherein Xaa is any amino acid residue).

A particularly preferred reverse peptide of and for use in the present invention has the amino acid sequence shown as SEQ ID NO: 4.

Peptides (including reverse peptides and fragments of either) of and for use in the invention may be generated wholly or partly by chemical synthesis or by expression from nucleic acid. The peptides of and for use in the present invention can be readily prepared according to well-established, standard liquid or, preferably, solid-phase peptide synthesis methods known in the art (see, for example, J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, N.Y. (1984).

Multimeric Peptides

As described above, the peptides may be in the form of multimers. Thus multimers (of 2, 3 or more individual kinestatin analogue monomeric units) are within the scope of the invention.

Such multimers may be used to prepare a monomeric peptide by preparing a multimeric peptide that includes the monomeric unit, and a cleavable site (i.e., an enzymatically cleavable site), and then cleaving the multimer to yield a desired monomer.

The use of multimers can increase the binding affinity for a receptor. Thus, in the present case, the binding affinity of the peptides of the invention to the bradykinin $B_2$ receptor, can often be increased by using multimers of 2-5, preferably 2-3 receptor binding moieties.

The multimers can be homomers or heteromers. As used herein, the term homomer, refers to a multimer containing only polypeptides corresponding to the amino acid sequence of SEQ ID NO:1 or fragments, variants, splice variants, fusion proteins, or other kinestatin analogs described herein). These homomers may contain kinestatin peptides having identical or different amino acid sequences. For example, the multimers can include only kinestatin peptides having an identical amino acid sequence, or can include different amino acid sequences. The multimer can be a homodimer (e.g., containing kinestatin peptides having identical or different amino acid sequences), homotrimer or homotetramer.

As used herein, the term heteromer refers to a multimer containing one or more heterologous polypeptides (i.e., non-kinestatin peptides) in addition to the kinestatin peptides described herein.

The multimers may be the result of hydrophobic, hydrophilic, ionic and/or covalent associations and/or may be indirectly linked, by for example, liposome formation. Thus, in one embodiment, multimers are formed when the kinestatin peptides described herein contact one another in solution. In another embodiment, heteromultimers are formed when kinestatin and non-kinestatin peptides contact antibodies to the polypeptides described herein (including antibodies to the heterologous polypeptide sequence in a fusion protein described herein) in solution. In other embodiments, multimers described herein may be formed by covalent associations with and/or between the kinestatin peptides (and optionally non-kinestatin peptides) described herein.

Such covalent associations can involve one or more amino acid residues contained in the kinestatin sequence (e.g., that recited in SEQ ID NO:1). In one embodiment, the covalent associations are the consequence of chemical or recombinant manipulation. Alternatively, such covalent associations can involve one or more amino acid residues contained in the heterologous polypeptide sequence in a kinestatin fusion protein. In one example, covalent associations are between the heterologous sequence contained in a fusion protein described herein (see, e.g., U.S. Pat. No. 5,478,925). In a specific example, the covalent associations are between the heterologous sequence contained in a kinestatin-Fc fusion protein described herein. In another specific example, covalent associations of fusion proteins described herein are between heterologous polypeptide sequence from another protein that is capable of forming covalently associated multimers, for example, oseteoprotegerin (see, e.g., International Publication NO: WO 98/49305). In another embodiment, two or more polypeptides described herein are joined through peptide linkers. Examples include those peptide linkers described in U.S. Pat. No. 5,073,627. Proteins comprising multiple kinestatin peptides separated by peptide linkers can be produced using conventional recombinant DNA technology.

Multimers may also be prepared by fusing the kinestatin peptides to a leucine zipper or isoleucine zipper polypeptide sequence. Among the known leucine zippers are naturally occurring peptides and derivatives thereof that dimerize or trimerize. Examples of leucine zipper domains suitable for producing soluble multimeric proteins described herein are those described in PCT application WO 94/10308. Recombinant fusion proteins comprising a polypeptide described herein fused to a polypeptide sequence that dimerizes or trimerizes in solution can be expressed in suitable host cells, and the resulting soluble multimeric fusion protein can be recovered from the culture supernatant using techniques known in the art.

The multimers may also be generated using chemical techniques known in the art. For example, polypeptides desired to be contained in the multimers described herein may be chemically cross-linked using linker molecules and linker molecule length optimization techniques known in the art (see, e.g., U.S. Pat. No. 5,478,925). Additionally, the multimers can be generated using techniques known in the art to form one or more inter-molecule cross-links between the cysteine residues located within the sequence of the polypeptides desired to be contained in the multimer (see, e.g., U.S. Pat. No. 5,478,925). Further, polypeptides described herein may be routinely modified by the addition of cysteine or biotin to the C-terminus or N-terminus of the polypeptide and techniques known in the art may be applied to generate multimers containing one or more of these modified polypeptides (see, e.g., U.S. Pat. No. 5,478,925). Additionally, techniques known in the art can be used to prepare liposomes containing two or more kinestatin peptides desired to be contained in the multimer (see, e.g., U.S. Pat. No. 5,478,925,).

Alternatively, those multimers including only naturally-occurring amino acids can be formed using genetic engineering techniques known in the art. Alternatively, those that include post-translational or other modifications can be prepared by a combination of recombinant techniques and chemical modifications. In one embodiment, the kinestatin peptides are produced recombinantly using fusion protein technology described herein or otherwise known in the art (see, e.g., U.S. Pat. No. 5,478,925, which is herein incorporated by reference inlits entirety). For example, polynucleotides coding for a homodimer described herein can be generated by ligating a polynucleotide sequence encoding a kinestatin peptide described herein to sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925). The recombinant techniques described herein or otherwise known in the art can be applied to generate recombinant kinestatin peptides that contain a transmembrane domain (or hydrophobic or signal peptide) and that can be incorporated by membrane reconstitution techniques into liposomes (see, e.g., U.S. Pat. No. 5,478,925).

Pro-Drugs

The peptides described herein are intended, at least in some embodiments, to be administered to a human or other mammal to treat or prevent a disorder mediated by bradykinin release. Peptides are typically administered parenterally, and may be readily metabolized by plasma proteases. Oral administration, which is perhaps the most attractive route of administration, may be even more problematic. In the stomach, acid degrades and enzymes break down the peptides. Those peptides that survive to enter the intestine intact are subjected to additional proteolysis as they are continuously barraged by a variety of enzymes, including gastric and pancreatic enzymes, exo- and endopeptidases, and brush border peptidases. As a result, passage of peptides from the lumen of the intestine into the bloodstream can be severely limited. However, various prodrugs have been developed that enable parenteral and oral administration of therapeutic peptides.

Peptides can be conjugated to various moieties, such as polymeric moieties, to modify the physiochemical properties of the peptide drugs, for example, to increase resistance to acidic and enzymatic degradation and to enhance penetration of such drugs across mucosal membranes. For example, Abuchowski and Davis have described various methods for derivatizating enzymes to provide water-soluble, non-immunogenic, in vivo stabilized products ("Soluble polymers-Enzyme adducts," Enzymes as Drugs, Eds. Holcenberg and Roberts, J. Wiley and Sons, New York, N.Y. (1981)). Abuchowski and Davis discuss various ways of conjugating enzymes with polymeric materials, such as dextrans, polyvinyl pyrrolidones, glycopeptides, polyethylene glycol and polyamino acids. The resulting conjugated polypeptides retain their biological activities and solubility in water for parenteral applications.

U.S. Pat. No. 4,179,337 to Davis, et al. teaches coupling peptides to polyethylene glycol or polypropylene glycol having a molecular weight of 500 to 20,000 Daltons to provide a physiologically active non-immunogenic water soluble polypeptide composition. The polyethylene glycol or polypropylene glycol protects the polypeptide from loss of activity and the composition can be injected into the mammalian circulatory system with substantially no immunogenic response.

U.S. Pat. Nos. 5,681,811, 5,438,040 and 5,359,030 teach stabilized, conjugated polypeptide complexes including a therapeutic agent coupled to an oligomer that includes lipophilic and hydrophilic moieties. Garmen, et al. describe a protein-PEG prodrug (Garman, A. J., and Kalindjian, S. B., *FEBS Lett.*, 1987, 223, 361-365). A prodrug can be prepared using this chemistry, by first preparing a maleic anhydride reagent from polydispersed MPEG5000 and then conjugating this reagent to the peptides disclosed herein. The reaction of amino acids with maleic anhydrides is well known. The hydrolysis of the maleyl-amide bond to reform the amine-containing drug is aided by the presence of the neighboring free carboxyl group and the geometry of attack set up by the double bond. The peptides can be released (by hydrolysis of the prodrugs) under physiological conditions.

The peptides can also be coupled to polymers, such as polydispersed PEG, via a degradable linkage, for example, the degradable linkage shown (with respect to pegylated interferon α-2b) in Roberts, M. J., et al., *Adv. Drug Delivery Rev.*, 2002, 54, 459-476.

The peptides can also be linked to polymers such as PEG using 1,6 or 1,4 benzyl elimination (BE) strategies (see, for example, Lee, S., et al., *Bioconjugate Chem.*, (2001), 12, 163-169; Greenwald, R. B., et al., U.S. Pat. No. 6,180,095, 2001; Greenwald, R. B., et al., J. Med. Chem., 1999, 42, 3657-3667.); the use of trimethyl lock lactonization (TML) (Greenwald, R. B., et al., J. Med. Chem., 2000, 43, 475-487); the coupling of PEG carboxylic acid to a hydroxy-terminated carboxylic acid linker (Roberts, M. J., J. Pharm. Sci., 1998, 87(11), 1440-1445), and PEG prodrugs involving families of MPEG phenyl ethers and MPEG benzamides linked to an amine-containing drug via an aryl carbamate (Roberts, M. J., et al., Adv. Drug Delivery Rev., 2002, 54, 459-476), including a prodrug structure involving a meta relationship between the carbamate and the PEG amide or ether (U.S. Pat. No. 6,413, 507 to Bently, et al.); and prodrugs involving a reduction mechanism as opposed to a hydrolysis mechanism (Zalipsky, S., et al., Bioconjugate Chem., 1999, 10(5), 703-707).

The peptides have free amino, amido, hydroxy and/or carboxylic groups and these functional groups can be used to convert the peptides into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of various polymers, for example, polyalkylene glycols such as polyethylene glycol. Prodrugs also include compounds wherein carbonates, carbamates, amides and alkyl esters which are covalently bonded to the above peptides through the C-terminal carboxylic acids.

Some approaches involve using enzyme inhibitors to slow the rate of degradation of proteins and peptides in the gastrointestinal tract; manipulating pH to inactivate local digestive enzymes; using permeation enhancers to improve the absorption of peptides by increasing their paracellular and transcellular transports; using nanoparticles as particulate carriers to facilitate intact absorption by the intestinal epithelium, especially, Peyer's patches, and to increase resistance to enzyme degradation; liquid emulsions to protect the drug from chemical and enzymatic breakdown in the intestinal lumen; and micelle formulations for poorly water-solubulized drugs.

In some cases, the peptides can be provided in a suitable capsule or tablet with an enteric coating, so that the peptide is not released in the stomach. Alternatively, or additionally, the peptide can be provided as a prodrug. In one embodiment, the peptides are present in these drug delivery devices as prodrugs.

Prodrugs comprising the peptides of the invention or prodrugs from which peptides of the invention (including analogues and fragments) are released or are releaseable are considered to be analogues of the invention.

Isotopically-labelled peptides or peptide prodrug are also encompassed by the invention. Such peptides or peptide prodrugs are identical to the. peptides or peptide prodrugs of the invention, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, and $^{35}$S, respectively. Peptides of the present invention, prodrugs thereof, and/or the prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled peptides and prodrugs thereof can generally be prepared by carrying out readily known procedures, including substituting a readily available isotopically-labeled reagent for a non-isotopically-labeled reagent, e.g., a labeled amino acid.

Peptidomimetics

The present invention further encompasses mimetic peptides of kinestatin which can be used as therapeutic peptides. Mimetic kinestatin peptides are short peptides which mimic the biological activity of kinestatin by binding to the bradykinin $B_2$ receptor and functioning as an antagonist at that receptor. Such mimetic peptides can be obtained from methods known in the art such as, but not limited to, phage display or combinatorial chemistry. For example, the method disclosed by Wrighton, et al., *Science* 273:458-463 (1996) can be used to generate mimetic kinestatin peptides.

Nucleic Acid

Alternatively, peptides of and for use in the present invention may be produced by use of nucleic acid in an expression system.

Accordingly the present invention also provides in various aspects nucleic acid encoding peptides of the invention.

For example, in one aspect, the invention further provides an isolated polynucleotide encoding the peptide(which may be a reverse peptide kinestatin) of the present invention.

In a preferred embodiment, the polynucleotide comprises the nucleic acid sequence:

```
CAAATTCCTGGTTTAGGCCCTCTGCGT.    (SEQ ID NO: 5)
```

Generally, nucleic acid according to the present invention is provided as an isolate, in isolated and/or purified form, or free or substantially free of material with which it is naturally associated, such as free or substantially free of nucleic acid flanking the gene in the toad genome, except possibly one or more regulatory sequence (s) for expression. Nucleic acid may be wholly or partially synthetic and may include genomic DNA, cDNA or RNA.

Nucleic acid sequences encoding a peptide in accordance with the present invention can be readily prepared by the skilled person using the information and references contained herein and techniques known in the art (for example, see Sambrook, Fritsch and Maniatis, "Molecular Cloning, A Laboratory Manual, Cold Spring Harbor Laboratory Press, 1989, and Ausubel et al, Short Protocols in Molecular Biology, John Wiley and Sons, 1992).

Modifications to the sequences can be made, e. g. using site directed mutagenesis, to lead to the expression of modified peptide or to take account of codon preference in the host cells used to express the nucleic acid.

In order to obtain expression of the nucleic acid sequences, the sequences can be incorporated in a vector having one or more control sequences operably linked to the nucleic acid to control its expression. The vectors may include other sequences such as promoters or enhancers to drive the expression of the inserted nucleic acid, nucleic acid sequences so that the peptide is produced as a fusion and/or nucleic acid encoding secretion signals so that the polypeptide produced in the host cell is secreted from the cell.

Peptides can then be obtained by transforming the vectors into host cells in which the vector is functional, culturing the host cells so that the peptide is produced and recovering the peptide from the host cells or the surrounding medium.

Thus, the present invention also encompasses a method of making a peptide (as disclosed), the method including expression from nucleic acid encoding the peptide (generally nucleic acid according to the invention). This may conveniently be achieved by growing a host cell in culture, containing such a vector, under appropriate conditions which cause or allow expression of the polypeptide.

Suitable vectors can be chosen or constructed, containing appropriate regulatory sequences, including promoter sequences, terminator fragments, polyadenylation sequences, enhancer sequences, marker genes and other sequences as appropriate.

Vectors may be plasmids, viral e. g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Systems for cloning and expression of a polypeptide in a variety of different host cells are well known. Suitable host cells include bacteria, eukaryotic cells such as mammalian and yeast, and baculovirus systems.

Thus, a further aspect of the present invention provides a host cell containing heterologous nucleic acid as disclosed herein.

The nucleic acid of the invention may be integrated into the genome (e. g. chromosome) of the host cell;

Integration may be promoted by inclusion of sequences which promote recombination with the genome, in accordance with standard techniques. The nucleic acid may be on an extra-chromosomal vector within the cell, or otherwise identifiably heterologous or foreign to the cell. The introduction, which may (particularly for in vitro introduction) be generally referred to without limitation as "transformation", may employ any available technique.

For eukaryotic cells, suitable techniques may include calcium phosphate transfection, DEAE-Dextran, electroporation, liposome-mediated transfection and transduction using retrovirus or other virus, e. g. vaccinia or, for insect cells, baculovirus. For bacterial cells, suitable techniques may include calcium chloride transformation, electroporation and transfection using bacteriophage. As an alternative, direct injection of the nucleic acid could be employed.

The introduction may be followed by causing or allowing expression from the nucleic acid, e. g. by culturing host cells (which may include cells actually transformed although more likely the cells will be descendants of the transformed cells) under conditions for expression of the gene, so that the encoded polypeptide (or peptide) is produced. If the polypeptide is expressed coupled to an appropriate signal leader peptide it may be secreted from the cell into the culture medium. Following production by expression, a polypeptide or peptide may be isolated and/or purified from the host cell and/or culture medium, as the case may be, and subsequently used as desired, e. g. in the formulation of a composition which may include one or more additional components, such as a pharmaceutical composition which includes one or more pharmaceutically acceptable excipients, vehicles or carriers (e. g. see below).

Pharmaceutical Compositions

The invention further provides pharmaceutical compositions comprising the peptide (or analogue or fragment) of the invention. Pharmaceutical compositions according to the present invention, and for use in accordance with the present invention, may comprise, in addition to active ingredient, a pharmaceutically acceptable excipient, carrier, buffer stabiliser or other materials well known to those skilled in the art. Such materials should be non-toxic and should not interfere with the efficacy of the active ingredient. The precise nature of the carrier or other material will depend on the route of administration, which may be, for example, oral, intravenous, or topical.

The formulation may be a liquid, for example, a physiologic salt solution containing non-phosphate buffer at pH 6.8-7.6, or a lyophilised powder.

Dose

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

Administration

Peptides of and for use in the present invention may be administered alone but will preferably be administered as a pharmaceutical composition, which will generally comprise a suitable pharmaceutical excipient, diluent or carrier selected dependent on the intended route of administration.

The peptides may be administered to a patient in need of treatment via any suitable route. The precise dose will depend upon a number of factors, including the precise nature of the peptide.

Some suitable routes of administration include (but are not limited to) oral, rectal, nasal, topical (including buccal and sublingual), vaginal or parenteral (including subcutaneous, intramuscular, intravenous, intradermal, intrathecal and epidural) administration.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The composition may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Implantable or microcapsular sustained release matrices include polylactides (U.S. Pat. No. 3,773,919; EP-A-0058481) copolymers of L-glutamic acid and gamma ethyl-L-glutamate (Sidman et al, Biopolymers 22(1): 547-556, 1985)., poly (2-hydroxyethyl-methacrylate) or ethylene vinyl acetate (Langer et al, J. Biomed. Mater. Res. 15: 167-277, 1981, and Langer, Chem. Tech. 12:98-105, 1982). Liposomes containing the polypeptides are prepared by well-known methods: DE 3,218, 121A; Epstein et al, PNAS USA, 82: 3688-3692, 1985; Hwang et al, PNAS USA, 77: 4030-4034, 1980; EP-A-0052522; E-A-0036676; EP-A-0088046; EP-A-0143949; EP-A-0142541; JP-A-83-11808; U.S. Pat. Nos. 4,485,045 and 4,544,545. Ordinarily, the liposomes are of the small (about 200-800 Angstroms) unilamellar type in which the lipid content is greater than about 30 mol. % cholesterol, the selected proportion being adjusted for the optimal rate of the polypeptide leakage.

Examples of the techniques and protocols mentioned above and other techniques and protocols which may be used in accordance with the invention can be found in Remington's Pharmaceutical Sciences, 16th edition, Oslo, A. (ed), 1980.

Targeting therapies may be used to deliver the active agent e.g. peptide more specifically to arterial smooth muscle, by the use of targeting systems such as antibody or cell specific ligands.

Therapeutic Uses

The peptides of the invention may be used bradykinin antagonists for the control and/or treatment of a wide variety of clinical conditions in mammals, including humans. The peptides and methods of the invention may be used in the treatment of any condition or disorder for which bradykinin antagonists and/or vasoconstrictors may be useful.

"Treatment" or "therapy" includes any regime that can benefit a human or non-human animal. The treatment may be in respect of an existing condition or may be prophylactic (preventative treatment). Treatment may include curative, alleviation or prophylactic effects.

The peptides may be used in any condition for which antagonism of bradykinin receptors, inhibition of angiogenesis and/or constriction of vessels may be therapeutically useful.

In a preferred embodiment, the peptides are used for the treatment of cardiovascular disorders such as hypotension. Other conditions for which the peptides and methods of the invention may be useful include pain relief e.g. as an anti-inflammatory agent.

Other conditions which amyu be treated using the peptides and methods of the invention include inflammation and inflammatory disorders, cardiovascular disorders such as hypotension, pain, common cold, allergies and immunology/allergy disorders, asthma, pancreatitis, burns and other skin disorders, viral infection and other infectious diseases such as sepsis, multiple trauma and the like. Specific conditions include, but are not limited to, respiratory diseases, diuresis, natriuresis, calciuresis, COPD (chronic obstructive pulmonary disease), itching, cystitis, pruritis, rheumatoid arthritis, osteoarthritis, migraine, neuropathic pain, post-traumatic and post ischemic cerebral eczema, liver cirrhosis and other liver/kidney diseases, rhinitis, hepatorenal failure, diabetes and other metabolic diseases, metastasis, pancreatitis, neovascularization, corneal haze, glaucoma, ocular pain, ocular hypertension and other eye diseases, angio edema and the like in mammals, especially humans.

Further, bradykinin $B_2$ receptor activation is believed to be associated with some of the symptoms of Alzheimer's disease. Thus the peptides of the invention may be used as anti plaque forming agents in neurological or other degenerative disease. Examples of such disorders include, but are not limited to, Huntington's disease, Parkinson's disease and other central nervous system disorders such as amyotrophic lateral sclerosis, multiple sclerosis, stroke, head trauma, post-surgical brain edema, brain edema (general), cytotoxic brain edema (such as that associated with brain tumors, stroke, head trauma, etc.), brain edema associated with metabolic diseases (renal failure, pediatric metabolic diseases, etc.), brain tumor and other cancers, pseudotumor cerebri, hydrocephalus, spinal cord trauma, spinal cord edema, neurodegenerative diseases, post-traumatic brain injury, other head injuries, and the like.

Anti-Angiogenic Methods of Treatment

The peptides and methods of the invention may be used to inhibit angiogenesis. There are several methods for inhibiting angiogenesis. Angiogenesis can be inhibited by administering an effective amount of a suitable anti-angiogenic peptide of the invention to a patient in need of such treatment. The methods can be used to treat tumours, various. autoimmune disorders, hereditary disorders, ocular disorders and other angiogenesis-mediated disorders.

The therapeutic and diagnostic methods described herein typically involve administering an effective amount of the peptides or compositions including the peptides to a patient. The exact dose to be administered will vary according to the use of the compositions and on the age, sex and condition of the patient, and can readily be determined by the treating physician. The compositions may be administered as a single dose or in a continuous manner over a period of time. Doses-may be repeated as appropriate.

The compositions and methods can be used to treat angiogenesis-mediated disorders including hemangioma, solid tumors, leukemia, metastasis, telangiectasia, psoriasis, scleroderma, pyogenic granuloma, myocardial angiogenesis, Crohn's disease, plaque neovascularization, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, Helicobacter related diseases, fractures, keloids, and vasculogenesis. Specific disorders that can be treated, and compounds and compositions useful in these methods, are described in more detail below.

Carcinomas/Tumors

Carcinomas that may be treated using the peptides, compounds, compositions and methods of the invention include colorectal carcinoma, gastric carcinoma, signet ring type, esophageal carcinoma, intestinal type, mucinous type, pancreatic carcinoma, lung. carcinoma, breast carcinoma, renal carcinoma, bladder carcinoma, prostate carcinoma, testicular carcinoma, ovarian carcinoma, endometrial carcinoma, thyroid carcinoma, liver carcinoma, larynx carcinoma, mesothelioma, neuroendocrine carcinomas, neuroectodermal tumors, melanoma, gliomas, neuroblastomas, sarcomas, leiomyosarcoma, MFII, fibrosarcoma, liposarcoma, MPNT, chondrosarcoma, and lymphomas.

Ocular Disorders Mediated by Angiogenesis

Various ocular disorders are mediated by angiogenesis, and may be treated using the compounds, compositions and methods described herein. One example of a disease mediated by angiogenesis is ocular neovascular disease, which is characterized by invasion of new blood vessels into the structures of the eye and is the most common cause of blindness. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, atopic keratitis, superior limbic keratitis, pterygium keratitis sicca, periphigoid radial keratotomy, and corneal graph rejection. Diseases associated with retinal/choroidal neovascularization include, but are not limited to, diabetic retinopathy, macular degeneration, presumed myopia, optic pits, chronic retinal detachment, hyperviscosity syndromes, trauma and post-laser complications. Other diseases include, but are not limited to, diseases associated with rubeosis (neovascularization of the angle) and diseases caused by the abnormal proliferation of fibrovascular or fibrous tissue including all forms of proliferative vitreoretinopathy.

Inflammation

The peptides and methods of the invention may also be used to treat angiogenesis-mediated disorders, such as inflammation, including various forms of arthritis, such as rheumatoid arthritis and osteoarthritis. In these methods, treatment with combinations of the compounds described herein with other agents useful for treating the disorders, such as cyclooxygenase-2 (COX-2) inhibitors, which are well known to those of skill in the art.

The blood vessels in the synovial lining of the joints can undergo angiogenesis. The endothelial cells form new vascular networks and release factors and reactive oxygen species that lead to pannus growth and cartilage destruction. These factors are believed to actively contribute to rheumatoid arthritis and also to osteoarthritis. Chondrocyte activation by angiogenic-related factors-contributes to joint destruction, and also promotes new bone formation. The methods described herein can be used as a therapeutic intervention to prevent bone destruction and new bone formation.

Pathological angiogenesis is also believed to be involved with chronic inflammation. Examples of disorders that can be treated using the compounds, compositions and methods described herein include ulcerative colitis, Crohn's disease, bartonellosis, and atherosclerosis.

In treating a specific disease using a peptide or method of the invention, in the treatment of a specific disease, the peptidess of the present invention may be combined with various existing therapeutic agents used for that disease.

In some embodiments, the kinestatin peptide can exhibit more effective therapeutic effects when used in combination with an $H_1$-antagonist. Accordingly, in one embodiment, the pharmaceutical compositions comprise a therapeutically effective amount of kinestatin, an analogue thereof or a prodrug thereof as described herein and an $H_1$-antagonist or pharmaceutically acceptable salt thereof, and a pharmaceutically acceptable carrier.

The combination of a kinestatin peptide as described herein with an anti-histamine ($H_1$ antagonist) can be particularly favored for use in the prophylaxis and treatment of asthma and rhinitis. Examples of anti-histamines are chlorpheniramine, brompheniramine, clemastine, ketotifen, azatadine, loratadine, terfenadine, cetirizine, astemizole, tazifylline, levocabastine, diphenhydramine, temelastine, etolotifen, acrivastine, azelastine, ebastine, mequitazine, KA-398, FK-613, mizolastine, MDL-103896, levocetirizine, mometasone furoate, DF-1111301, KC-11404, carebastine, ramatroban, desloratadine, noberastine, selenotifen, alinastine, E-4716, efletirizine, tritoqualine, norastemizole, ZCR-2060, WY-49051, KAA-276, VWF-K-9015, tagorizine, KC-11425, epinastine, MDL-28163 terfenadine, HSR-609, acrivastine and BMY-25368.

The kinestatin peptides may advantageously be employed in combination with one or more other therapeutic agents, including an antibiotic, anti-fungal, anti-viral, anti-histamine, non-steroidal anti-inflammatory drug or disease modifying anti-rheumatic drug.

For treating rheumatoid arthritis, the kinestatin peptides may be combined with agents such as TNF-alpha inhibitors, for example, anti-TNF monoclonal antibodies (such as Remicade, CDP-870 and $D_2 E_7$) and TNF receptor immunoglobulin molecules (such as Enbrel®), COX-2 inhibitors (such as meloxicam, celecoxib, rofecoxib, valdecoxib and etoricoxib) low dose methotrexate, leflunomide, hydroxychloroquine, d-penicillamine, auranofin or parenteral or oral gold.

The kinestatin peptides may also be used in combination with existing therapeutic agents for the treatment of osteoarthritis. Suitable agents to be used in combination include standard non-steroidal anti-inflammatory agents (hereinafter NTHE's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The kinestatin peptides may also be used in combination with anticancer agents such as endostatin and angiostatin or cytotoxic drugs such as adriamycin, daunomycin, cis-platinum, etoposide, taxol, taxotere and alkaloids, such as vincristine, farnesyl transferase inhibitors, VEGF inhibitors, and antimetabolites such as methotrexate.

The kinestatin peptides may also be used in combination with antiviral agents such as Viracept, AZT, aciclovir and famciclovir, and antisepsis compounds such as Zovant, tifacogin, NOX-100 and 13R270773.

The kinestatin peptides may also be used in combination with cardiovascular agents such as calcium channel blockers, lipid lowering agents such as stating, fibrates, beta-blockers, Ace inhibitors, Angiotensin-2 receptor antagonists and platelet aggregation inhibitors.

The kinestatin peptides may also be used in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, nicotine agonists, Dopamine agonists and inhibitors of neuronal nitric oxide synthase), and anti-Alzheimer's drugs such as donepezil, tacrine, COX-2 inhibitors, propentofylline or metryfonate.

The kinestatin peptides may also be used in combination with osteoporosis agents such as roloxifene, droloxifene, lasofoxifene or fosomax and immunosuppressant agents such as FK-506 and rapamycin.

The kinestatin peptides may be combined with one or more of the following: (a) leukotriene biosynthesis inhibitors: 5-lipoxygenase (5-LO) inhibitors and 5-lipoxygenase activating protein (FLAP) antagonists selected from the group consisting of zileuton; ABT-761; fenleuton; tepoxalin; Abbott-79175; Abbott-85761; N-(5-substituted)-thiophene-2alkylsulfonamides of Formula (5.2.8); 2,6-di-tert-butylphenol hydrazones of Formula (5.2.10); the class of methoxytetrahydropyrans which includes Zeneca ZD-2138 of Formula (5.2.11); the compound SB-210661 of Formula (5.2.12) and the class to which it belongs; the class of pyridinyl-substituted-2-cyanonaphthalene compounds to which L-739,010 belongs; the class of 2-cyanoquinoline compounds to which L-746,530 belongs; the classes of indole and quinoline compounds to which MK-591, MK-886, and BAY X 1005 belong; (b) receptor antagonists for leukotrienes $LTB_4$, $LTC_4$, $LTD_4$, and $LTE_4$ selected from the group consisting of the phenothiazin-3-one class of compounds to which L-651,392 belongs; the class of amidino compounds to which CGS-25019c belongs; the class of benzoxaolamines to which ontazolast belongs; the class of benzenacarboximidamides to which BIIL 2841260 belongs; and the classes of compounds to which zafirlukast, ablukast, montelukast, praniukast, verlukast (MK-679), RG-12525, Ro-2459913, iralukast (CGP 45715A), and BAY X 7195 belong; (c) PDE4 inhibitors including inhibitors of the isoform PDE4D; (d) 5-Lipoxygenase (5-LO) inhibitors; or 5-lipoxygenase activating protein (FLAP) antagonists; (e) dual inhibitors of 5-lipoxygenase (5-LO) and antagonists of platelet activating factor (PAF); (f) leukotriene antagonists (LTRAs) including antagonists of $LTB_4$, $LTC_4$, $LTD_4$, and $LTE_4$; (g) antihistaminic HL receptor antagonists including cetirizine, loratadine, desloratadine, fexofenadine, astemizole, azelastine, and chlorpheniramine; (h) gastroprotective $H_2$ receptor antagonists; (i) $alpha_1$- and $alpha_2$-adrenoceptor agonist vasoconstrictor sympathomimetic agents administered orally or topically for decongestant use, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (j) $alpha_1$- and $alpha_2$-adrenoceptor agonists in combination with inhibitors of 5-lipoxygenase (5-LO); (k) anticholinergic agents including ipratropium bromide; tiotropium bromide; oxitropium bromide; pirenzepine; and telenzepine; (I) [3- to $beta_4$-adrenoceptor agonists including metaproterenol, isoproterenol, isoprenaline, albuterol, salbutamol, formoterol, salmeterol, terbutaline, orciprenaline, bitolterol mesylate, and pirbuterol; (m) methylxanthanines including theophylline and aminophylline; (n) sodium cromoglycate; (o) muscarinic receptor (M1, M2, and M3) antagonists; (p) COX-1 inhibitors (NTHEs); COX-2 selective inhibitors including rofecoxib; and nitric oxide NTHEs; (q) insulin-like growth factor type I (IGF-1) mimetics; (r) ciclesonide; (s) inhaled glucocorticoids with reduced systemic side effects, including prednisone, prednisolone, flunisolide, triamcinolone acetonide, beclomethasone dipropionate, budesonide, fluticasone propionate, and mometasone furoate; (t) tryptase inhibitors; (u) platelet activating factor (PAF) antagonists; (v) monoclonal antibodies active against endogenous inflammatory entities; (w) IPL 576; (x) anti-tumor necrosis factor (TNF-alpha) agents including Etanercept, Infliximab, and D2E7; (y) DMARDs including Leflunomide; (z) TCR peptides; (aa) interleukin converting; enzyme (ICE) inhibitors; (bb) IMPDH inhibitors; (Cc) adhesion Tolecule iibitors including VLA-4 antagonists; (dd) icathepsins; (ee) MAP kinase inhibitors; (ff) glucose-6 phosphate dehydrogenase inhibitors; (hh) gold in the form of an aurothio group together with various hydrophilic groups; (ii) immunosuppressive agents, e.g., cyclosporine, azathioprine, and methotrexate; (j) anti-gout agenrts, e.g., colchicirne; (kk) xanthine oxidase inhibiitors, e.g., allopurinol; (ll) uricosuric agents, e.g., probenecid, sulfinpyrazone, and benzbromarone; (mm): antineoplastic agents, especially antimitotic drugs including the vinca alkaloids such as vliblastine and vicristine; (nn) growth hormone secretagogues; (oo) inhibitors of nmatrix metalloproteases (Ps), stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10) and stromelysin-3 (MMP-11); (pp) transformin growth factor (TGFP); (qq) plateiet-derived growth factor (PDGF); (rr) fibroblast growth factors e.g., basic fibroblast growth factor (BFGF); (ss) gianuloqyte macrophage colony Bjtimulating factor (GM-CSF); (tt) capsaicin cream; (uu) Taclykinin NK, and $NK_3$ receptor antagonists selerted from the group consisting of NKP-608C; SB-233412 (talnetant); and D-4418; and (vv) elastase inhibitors selected from the group consisting of UT-77 and ZD-0892.

Targeting

Targeting therapies may be used to deliver the active agent e.g. peptide more specifically to arterial smooth muscle, by using targeting systems such as antibody-or cell specific ligands. These targeting systems can be covalently linked to the peptide sequence, or to a drug delivery vehicle (such as a liposome, microsphere, microparticle, microcapsule and the like). The peptides can also be targeted to ischemic heart tissue or to growing tumor beds (both of which are associated with attached capillary beds) by incorporating the peptides into microparticles or other drug delivery vehicles that are suitably sized so that they pass through the veins but lodge in capillary beds. When lodged in the beds, the peptides can be locally released (rather than systemically released) at a location where they are most useful.

As described above, the present invention further extends to methods of gene therapy using the nucleotides of the present invention The invention will now be described further in the following non-limiting examples. Reference is made to the accompanying drawings in which:

BRIEF DESCRIPTION OF THE FIGURES

FIG. 3 illustrates the nucleotide sequence of full-length cDNA (SEQ ID NO:6) encoding a single copy of kinestatin (SEQ ID NO:7) at the C-terminus of the open-reading frame (boxed). The putative signal peptide (single-underlined), the maximakinin encoding sequence (double-underlined) and the stop codon (asterisk) are indicated.

EXAMPLES

Example 1

Kinestatin Identification, Isolation, Purification and Characterisation

Figure 1:
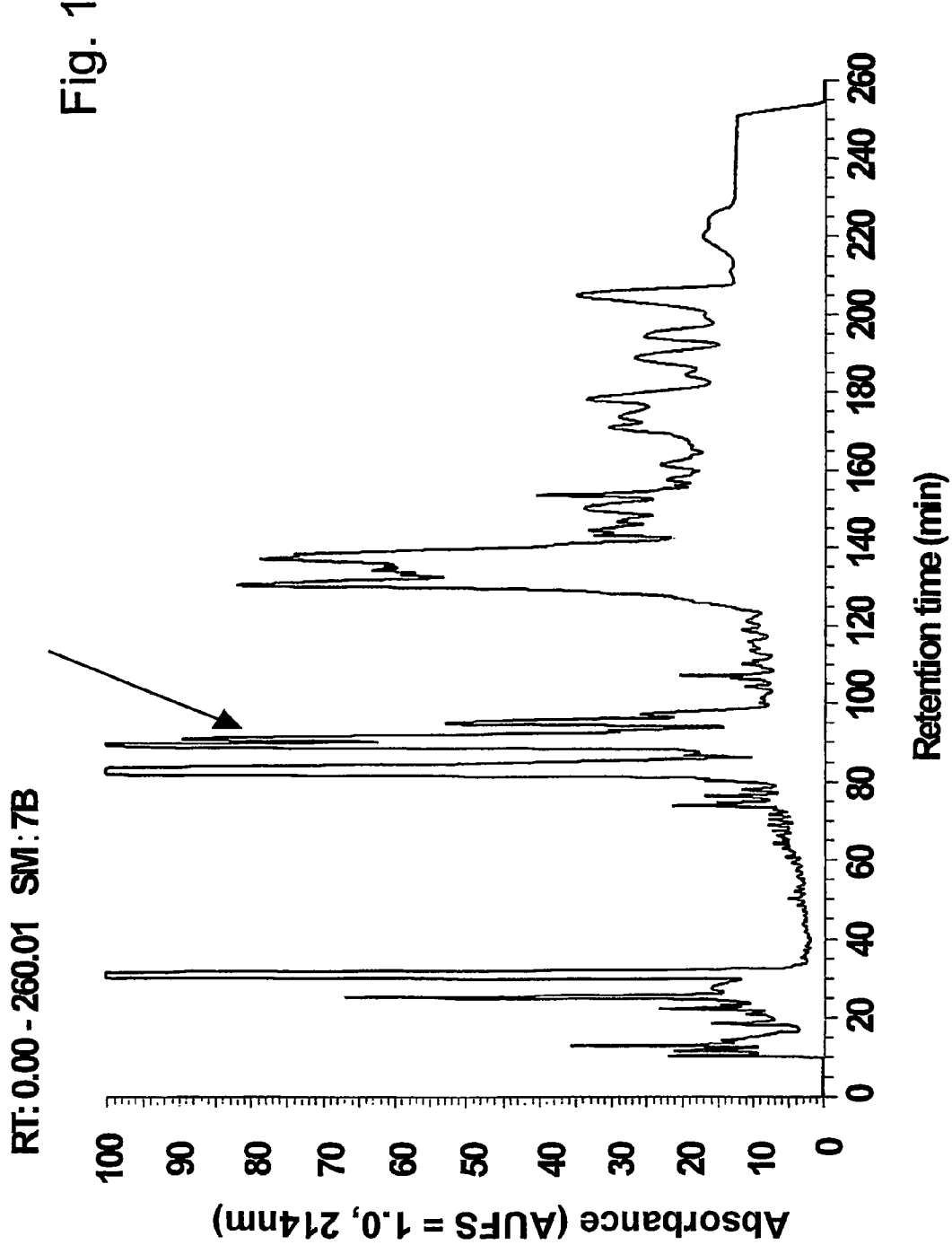
FIG. 1 illustrates absorbance profile of reverse-phase HPLC fractionated *Bombina maxima* skin secretion. The retention time of the bradykinin inhibitor peptide (kinestatin) is indicated by an arrow.

Materials and Methods
Acquisition of Toad Skin Secretion

Specimens of *Bombina maxima* (n=3) were obtained from a commercial source and were wild-caught in Yunnan Province in the People's Republic of China. Skin secretion was obtained by gentle massage of the dorsal skin surface and the paired paratoid and tibial glands for 2-3 min following which the induced secretion was obvious as a thick white foam. Secretions were washed from toads with distilled-deionised water, snap frozen in liquid nitrogen, lyophilised and stored at −20° C. prior to analysis.

Chromatographic Fractionation

Five milligrams of lyophilised skin secretion were dissolved in 0.5 ml of 0.05/99.95 (v/v) trifluoroacetic acid (TFA)/water and clarified of microparticulates by centrifugation. The supernatant was then subjected to reverse-phase HPLC fractionation using a Thermoquest gradient HPLC system fitted with a Jupiter semi-preparative C-5 column (30×1 cm). This was eluted with a linear gradient formed from 0.05/99.5 (v/v) TFA/water to 0.05/19.95/80.0 (v/v/v) TFA/water/acetonitrile in 240 min at a flow rate of 1 ml/min. Fractions (1 ml) were collected at minute intervals and the effluent absorbance was continuously monitored at λ214 nm. Samples (100 µl) were removed from each fraction.in triplicate, lyophilised and stored at −20° C. prior to smooth muscle pharmacological analysis.

Bioactivity Screening Using Material Smooth Muscle

Male albino Wistar rats (200-250 g) were euthanised by asphyxiation followed by cervical dislocation. The tail artery was prepared as described previously (Chen T et al, Peptides. 2002; 23:1547-1555, Chen T et al, Eur. J. Biochem. 2002; 269:4693-4700, Hirst et al Br. J. Radiol. 1994; 67:795-799). After perfusion of arterial preparations with $1\times10^{-5}$M phenylephrine to obtain constriction plateaux, relative relaxation was recorded as described below following applications of reconstituted 100 µl aliquots of HPLC fraction samples (1-240) from *B. maxima* skin secretion. This was carried out to exclude those fractions (25) containing direct arterial smooth muscle relaxant activity. Following this, remaining fractions (215) were employed in a protocol for the identification of bradykinin-potentiating peptides. The preparations were perfused as before with phenylephrine ($1\times10^{-5}$M) until constriction plateaux were obtained. Following this, combinations of phenylephrine ($1\times10^{-5}$M) and reconstituted non-myoactive fractions were perfused through individual preparations for 20 min. Immediately after this, the perfusate was replaced by a combination of phenylephrine ($1\times10^{-5}$M), bradykinin ($1\times10^{-6}$M) and reconstituted individual fractions. Changes in arterial smooth muscle tone were measured by a pressure transducer system and the percentage relative relaxations induced by bradykinin in the presence of reconstituted fractions were calculated using the MacLab computer package.

Structural Analyses

Peptides modulating bradykinin bioactivity, as determined by bioassay above, were subjected to MALDI-TOF analysis using a Perseptive Biosystems Voyager delayed-extraction instrument. Following determination of sample purity and the molecular mass of the $MN^+$ ion, peptides were subjected to MS/MS fragmentation and de novo sequence analysis using a Q-TOF Ultima mass spectrometer (Micromass, Manchester, UK).

Identification of cDNA Encoding the Novel Peptide

Dorsal skin was excised from a euthanised adult *B. maxima* toad, frozen in liquid nitrogen and subsequently ground to a fine powder in this medium. Polyadenylated mRNA was isolated using magnetic oligo-dT beads as described by the manufacturer (Dynal Biotec, UK). The isolated mRNA was subjected to a 3'-rapid amplification of cDNA ends (RACE) procedure using a SMART-RACE kit (Clontech UK) essentially as described by the manufacturer. A range of primers were employed to facilitate selection of sub-sets of clones and the sense primer employed (5'-AGTTCTCAGTGTCACT-TCCAGC-3') (SEQ ID NO:8) was designed to a region (bases 69-90) of the 5'-non-translated domain of the maximakinin transcript (EMBL accession no. AJ315488). The heterogeneous mixture of amplified transcripts was cloned using a pGEM-T vector system (Promega Corporation) and individual clones were sequenced using an ABI 3100 automated sequencer. This procedure was carried out prior to the current study as part of a larger programme of research involving systematic and parallel proteomic and genomic studies on amphibian skin peptides. The DNA sequence of each clone was translated in all possible 6 reading frames and archived on a customised FASTA database. This facilitated interrogation with primary structures of skin secretion peptides acquired either by conventional automated Edman degradation (ABI Procise 491 protein sequencer) or by MS/MS fragmentation de novo sequencing (Q-TOF Ultima).

Chemical Synthesis of the Novel Peptide

The novel peptide, named kinestatin, was synthesised by solid-phase fmoc chemistry using an Applied Biosystems 433 peptide synthesiser. The peptide was. purified by reverse phase HPLC and its purity and molecular mass were confirmed using mass spectroscopy.

Pharmacological Characterisation of Kinestatin Using Arterial Smooth Muscle

Arterial smooth muscle preparations were prepared as described previously and treated with phenylephrine ($1\times10^{-5}$M) until constriction plateaux were achieved. Following this a series of experiments were performed to address the pharmacological characterization of the novel peptide, kinestatin. 1) Separate dose response curves were constructed for bradykinin and kinestatin using concentrations of both peptides in the range of $10^{-11}$ to $10^{-5}$M. 2) The effect of prior addition of a range of concentrations of kinestatin on the observed activity of subsequently added bradykinin at its maximally effective concentration ($10^{-6}$M) was determined. 3) The effect of prior addition of kinestatin at its maximally inhibitory concentration ($10^{-8}$M) on a subsequent dose response study with bradykinin. 4) The effects of specific bradykinin $B_1$ receptor (desArg HOE 140) and $B_2$ receptor (HOE 140) (Sigma-Aldrich, UK) antagonists on both the bradykinin relaxation effect and the kinestatin antagonised bradykinin effect in the arterial-smooth muscle preparation. The preparations were prepared as described before. The stabilised artery segment was exposed to a $3\times10^{-7}$M concentration of either the $B_1$ receptor antagonist, desArg HOE 140, or the $B_2$ receptor antagonist, HOE 140, for 20 min. Following this, phenylephrine ($1\times10^{-5}$M) was added to the antagonist solution and perfused for 10 min to develop contraction of the arterial smooth muscle. On obtaining stable plateaux of constriction, the perfusate was replaced by another containing phenylephrine, antagonist and bradykinin ($1\times10^{-6}$M). During a 20 min perfusion period, changes in arterial pressure were recorded as described previously. In a second similar series of experiments, kinestatin ($1\times10^{-8}$M) was added to each of the specific bradykinin receptor sub-type antagonist solutions prior to the procedure described above. Data were analysed by computer using Students t test available on the Graph Pad Prism™ programme.

Results

Each specimen of *B. maxima*, yielded on average, 30-35 mg-dry-weight of skin secretion following stimulation. 5 mg of pooled secretion was subjected to reverse phase HPLC fractionation that produced a complex chromatogram (FIG. 1).

Figure 2:
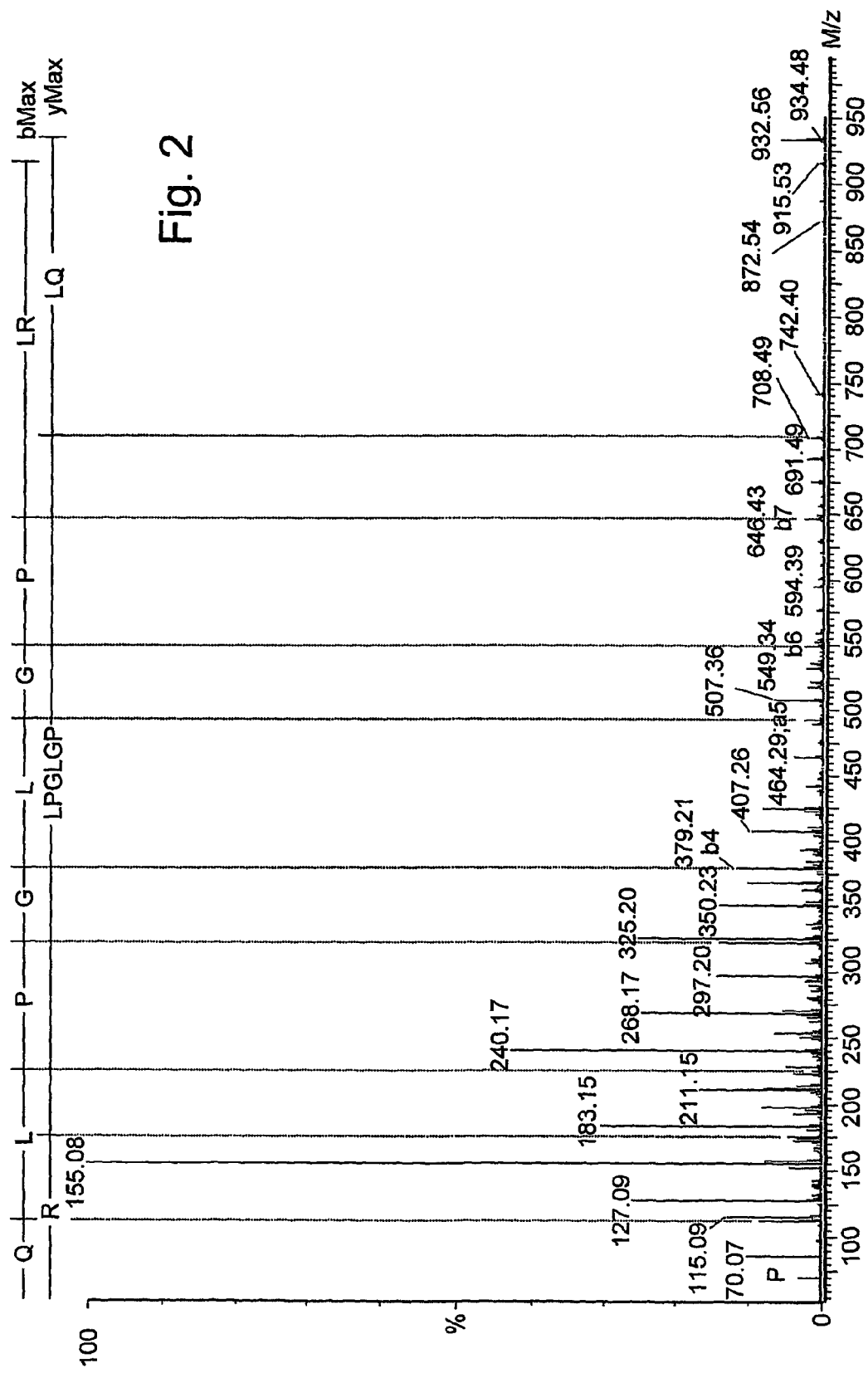
FIG. 2 illustrates Q-TOF Ultima MS/MS fragmentation profile of kinestatin with tabulated de novo sequence obtained using the embedded MaxENT™, PepSeq™ and MassSeq™ software. Isobaric Leu/Ile residues are not possible to differentiate and are assigned as Leu by default.

Screening of the chromatographic fractions (215) that were devoid of direct smooth muscle effects, failed to detect bradykinin-potentiating activity but identified a single peptide displaying bradykinin inhibitory activity. HPLC fraction #93 (see FIG. 1), containing the active peptide, was subjected to MALDI-TOF analysis that detected a single peptide of m/z 932.57. Subsequent analysis of the peptide on a Q-TOF Ultima mass spectrometer, confirmed the molecular mass of 932.57 Da as that of a singly-charged ion (M+H)+by isotopic resolution. The preliminary primary structure of the purified peptide was established by MS/MS fragmentation using the de novo sequencing software as: pGlu-Leu/Ile-Pro-Gly-Leu/Ile-Gly-Pro-Leu/Ile-Arg.amide (SEQ ID NO:9) (FIG. 2).

Interrogation of contemporary protein/peptide databases indicated little structural similarity with any known peptide or protein, except a limited degree with bradykinin nonapeptides (Table 1), none of which are N-terminally blocked or C-terminally amidated. By nature of its novel structure and bioactivity, this peptide was named kinestatin.

Interrogation of the custom translated database of cloned *B. maxima* skin cDNA with the non-post-translationally modified sequence of kinestatin, located this sequence at the C-terminus of a precursor open-reading frame of 116 amino acid residues (FIG. 3). This finding established that amino acid residue 2 was Ile and that residues 5 and 8 were Leu. The C-terminal residue of the open-reading frame was Gly. This can thus function as the amide donor for the generation of the argininamide residue on the mature peptide. The N-terminal residue was Gln, necessary for formation of the pyroglutamyl residue present in the mature peptide by post-translational modification. This residue was flanked upstream by a single arginyl residue, indicating a probable cleavage by propeptide convertase at this site. Identical, 116 amino acid residue precursor open-reading frames were present in three different sequenced clones and each contained, in addition to a single, C-terminally located copy of kinestatin, a single copy of the bradykinin-related nonadecapeptide, maximakinin (EMBL accession no. AJ440236), located upstream. Combination of the Q-TOF MS/MS data with the translated sequence from the cloned cDNA, unequivocally established the primary structure of kinestatin as: pGlu-Ile-Pro-Gly-Leu-Gly-Pro-Leu-Arg.amide (SEQ ID NO: 3).

The chemical synthesis of kinestatin was successful yielding 55 mg of peptide following purification. This synthetic replicate exhibited an identical mass and MS/MS fragmentation profile compared to the natural peptide.

Figure 4A:
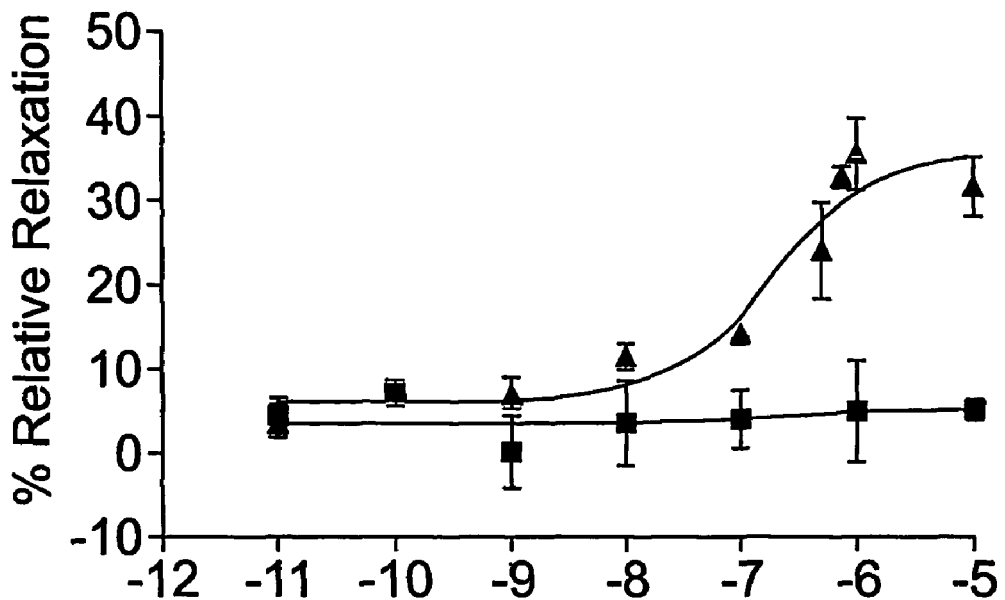
FIG. 4 illustrates comparative bioactivitiy profiles of bradykinin and kinestatin in the rat tail artery preparation. (A) Separate dose-responses of bradykinin (▲) and kinestatin (■). (B) Kinestatin dose-response (■) in the presence of maximal bradykinin relaxant concentration ($1\times10^{-6}$M) (▲). (C) Bradykinin dose-response (▲) and repeated in the presence of kinestatin ($1\times10^{-8}$M) (■). Each point represents the mean and standard error of six replicates.
Figure 4B:
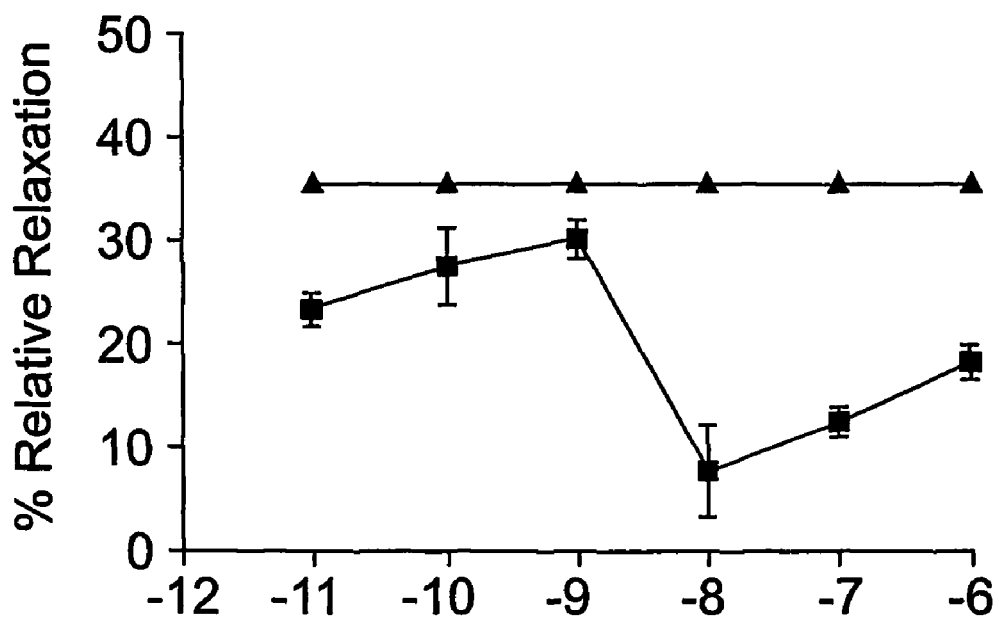
Figure 4C:
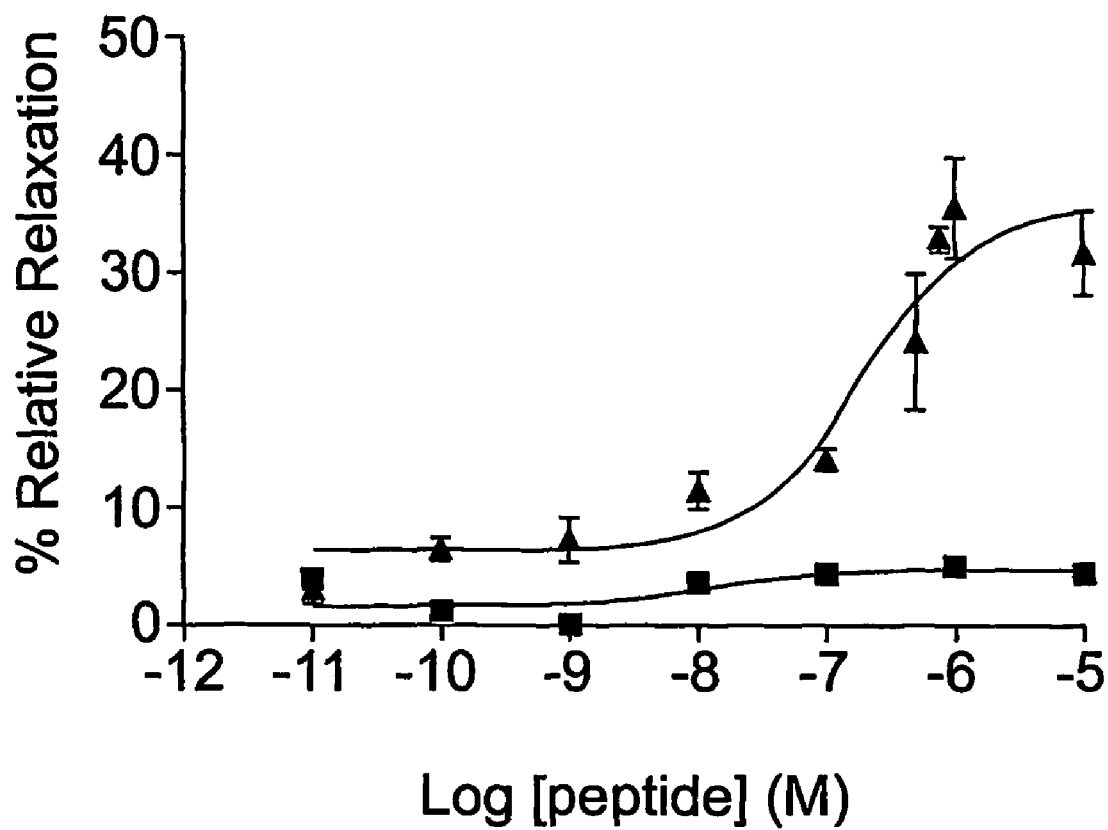
Figure 5A:
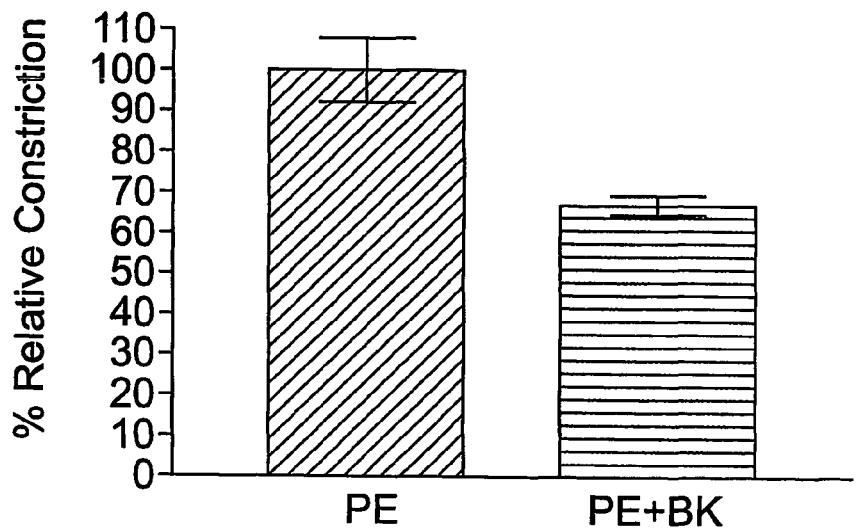
FIG. 5 illustrates pharmacological characterisation of the bradykinin-induced relaxation response in the phenylephrine pre-constricted rat tail artery preparation. PE—phenylephrine ($1\times10^{-5}$M), BK—bradykinin ($1\times10^{-6}$M) (A), HOE 140—$B_2$-receptor antagonist ($3\times10^{-7}$M) (B), d.Arg HOE 140—$B_1$-receptor antagonist ($3\times10^{-7}$M) (C). Each bar represents the mean and standard error of six replicates.
Figure 5B:
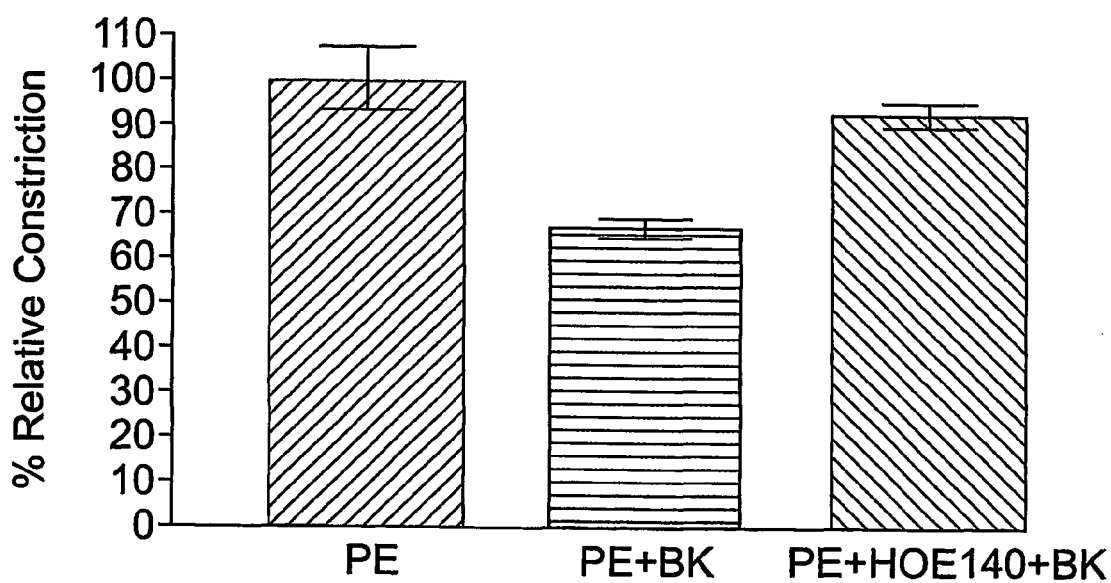
Figure 5C:
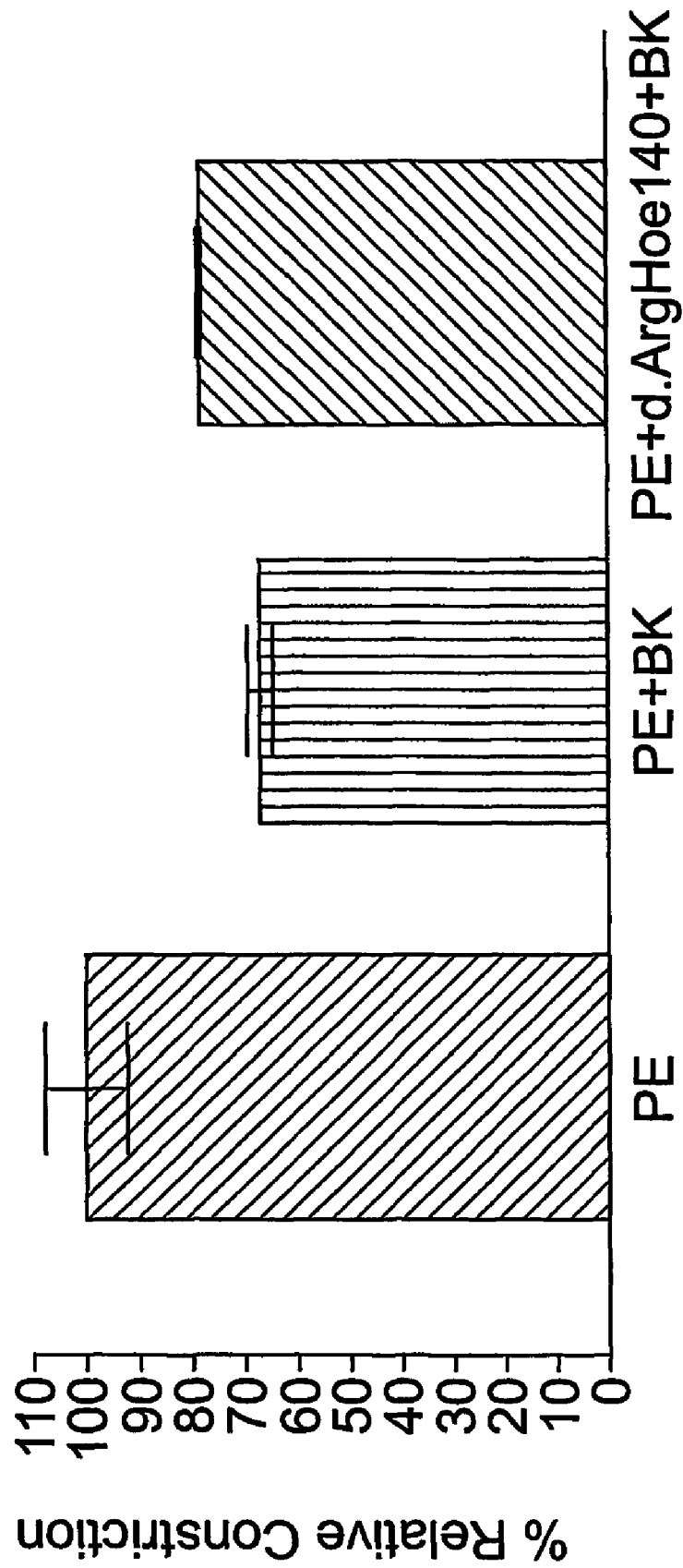
Figure 6A:
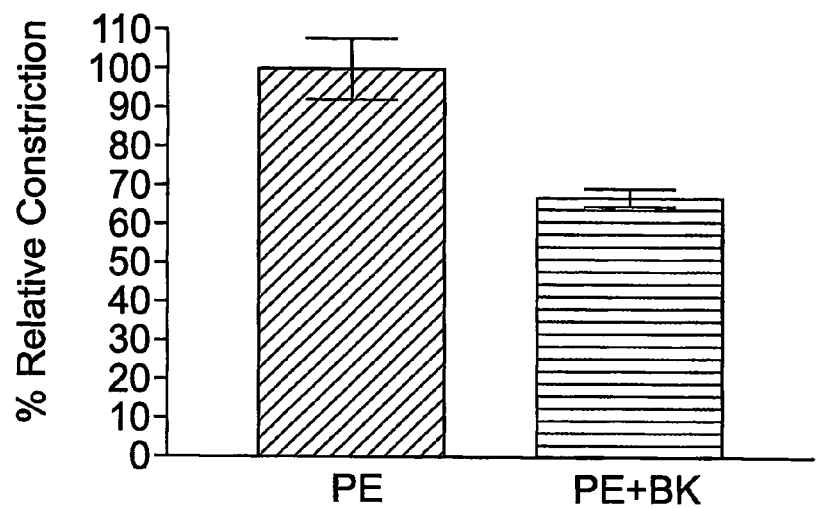
FIG. 6 illustrates the effect of kinestatin on bradykinin-induced relaxation of the phenylephrine pre-constricted rat tail artery preparation. PE—phenylephrine ($1\times10^{-5}$M), BK—bradykinin ($1\times10^{-6}$M) (A), KS—kinestatin ($1\times10^{-8}$M) (B). Each bar represents the mean and standard error of six replicates.
Figure 6B:
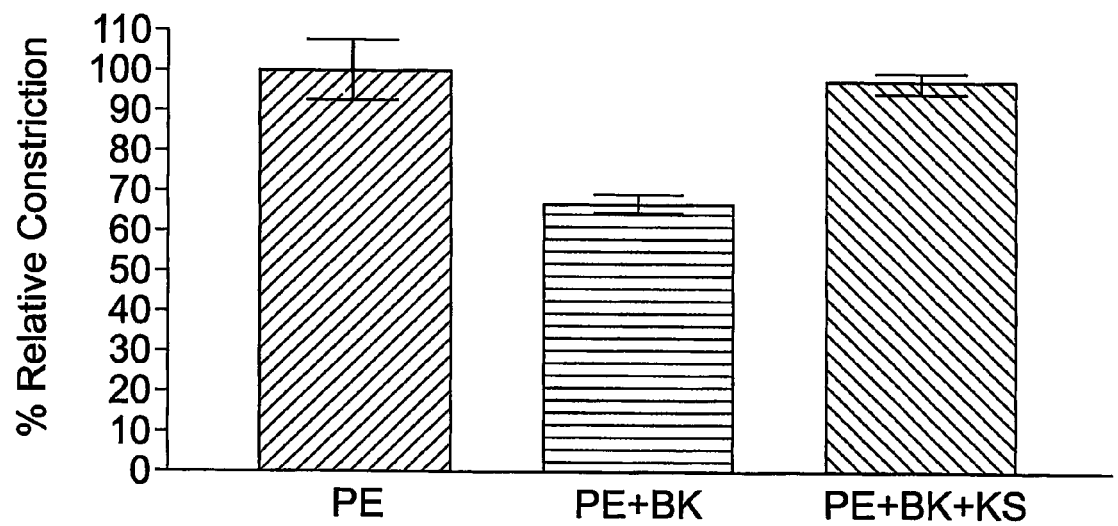
Figure 7A:
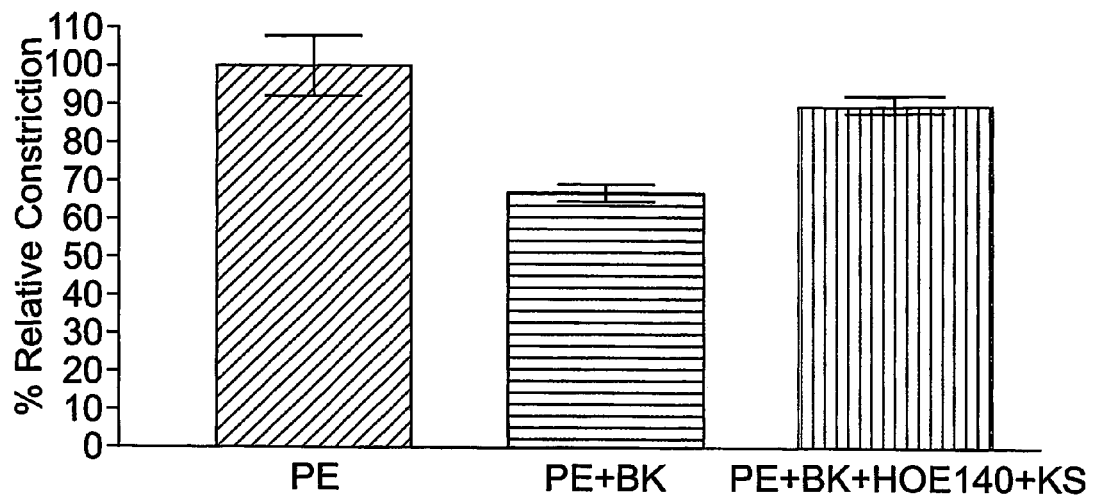
FIG. 7 illustrates the pharmacological characterisation of the kinestatin inhibitory response in the rat tail artery preparation. PE—phenylephrine ($1\times10^{-5}$M), BK—bradykinin ($1\times10^{-6}$M), HOE 140—$B_2$-receptor antagonist ($3\times10^{-7}$M) (A), d.Arg HOE 140—Bi-receptor antagonist ($3\times10^{-7}$M) (B), KS—kinestatin ($1\times10^{-8}$M). Each bar represents the mean and standard error of six replicates.
Figure 7B:
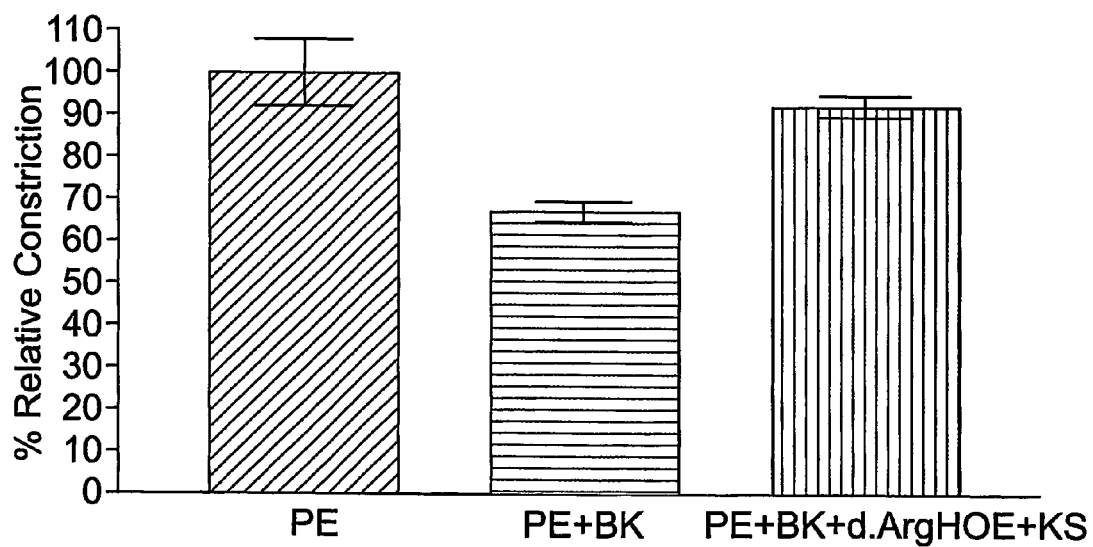

Repeat pharmacological experiments using the synthetic replicate of kinestatin and bradykinin in separate smooth muscle preparations, confirmed that it was devoid of myorelaxant activity in the effective molar concentration range of bradykinin (FIG. 4A). However, in a second series of experiments, in which smooth muscle preparations were pretreated with kinestatin, prior to application of bradykinin at its maximal effective concentration ($1 \times 10^{-6}$M), a dose-dependent inhibition of bradykinin-induced relaxation was observed by kinestatin in the range of $1 \times 10^{-9}$M-$1 \times 10^{-6}$M (FIG. 4B). Virtual total abolition of the bradykinin-induced relaxation dose response curve, was achieved in the presence of kinestatin at $1 \times 10^{-8}$M (FIG. 4C), a finding that was indicative of a non-competitive mechanism within this concentration range. The highly-specific bradykinin $B_2$ receptor antagonist, HOE-140, significantly inhibited (p=0.0247, n=6) the bradykinin-induced relaxation of the rat tail artery smooth muscle, whereas the same concentration ($3 \times 10^{-7}$M), of des Arg HOE 140 (a specific bradykinin $B_1$ receptor antagonist) had no significant effect (FIG. 5). These data indicated, as expected, that the bradykinin-induced relaxation of the arterial smooth muscle was mediated by $B_2$ receptors. In a similar experiment, carried out following addition of kinestatin ($1 \times 10^{-8}$M), both HOE 140 and des Arg HOE 140-treated preparations exhibited a significant inhibition of the bradykinin-induced relaxation (p=0.0015 and p=0.033, n=6, respectively) (FIGS. 6 and 7). These data indicate that kinestatin effects inhibition of the bradykinin-induced relaxation response in this arterial smooth muscle preparation by antagonism at $B_2$ receptors.

Discussion

The dermal granular glands of the dorsal skin of *Bombina maxima*, synthesise and secrete a complex defensive secretion that includes a novel bradykinin $B_2$ receptor antagonist peptide, named kinestatin. This peptide may represent the prototype of a new class of amphibian skin peptide due to its discrete bioactivity and primary structure.

The kinin/kininogen system is a favoured target for certain venom/defensive secretion components of both invertebrates and vertebrates. Arthropods and amphibians produce bradykinins in high concentrations and in the former group, where venom is injected, these are thought to play a central role in the pain, reddening and oedema associated with envenomation (Pisano, J. J. (1966). Mem. Inst. Butantan Simp. Internac. 33, 441-446). Amphibians produce bradykinin and a large array of related peptides in their defensive skin secretions and current evidence may suggest that the plethora of structural forms reflects targeting to different groups of predators. In contrast, the bradykinin-potentiating peptides of haemotoxic snake venoms (Higuchi et al. (1999) Immunopharmacology 44, 129-135), more recently discovered in scorpion venom (Meki, A. R. M. A., Nassar, A. Y. and Rochat, H. (1995) Peptides 16, 1359-1365), act as inhibitors of angiotensin-converting enzyme (ACE), a major bradykinin deactivating protease.

The discovery of kinestatin in the defensive skin secretion of *Bombina maxima*, thus reflects a novel target within the same kinin/kininogen system—selective bradykinin receptor antagonism. Bradykinin has maximal relaxing activity in the rat tail arterial smooth muscle preparation at a concentration of one micromolar. This can be almost totally blocked by ten nanomolar kinestatin, indicative of a possible higher affinity for and/or occupancy of bradykinin receptors. Subsequently, more discrete pharmacological characterisation experiments using the rat tail arterial smooth muscle preparation, indicated that the bradykinin-induced relaxation effect and its kinetensin-induced antagonism were mediated via $B_2$-receptors in a non-competitive fashion.

Comparison of the primary structures of kinestatin and those of previously identified amphibian skin bradykinins (Table 1) reveals a limited structural homology. Residues 4 (Gly), 7 (Pro) and 9 (Arg) are fully-conserved in all of these peptides. Residues 1 (pGlu), 2 (Ile), 5 (Leu) and 6 (Gly) are unique to kinestatin. Residue 3 (Pro) is conserved in most bradykinins and Leu at position 8 is found in the bradykinin from pickerel frog (Rana palustris) skin (Basir, Y. J., Knoop, F. C., Dulka, J. and Conlon, J. M. (2000). Biochim. Biophys. Acta.—Protein Structure and Molecular Enzymology 1543, 95-105).

Previous pharmacological studies have shown that $Leu^8$-bradykinin is devoid of bradykinin agonist activity but that in $B_1$-receptor-rich preparations, such as the rabbit aorta, it is a potent antagonist to both bradykinin and the selective $B_1$-receptor agonist, des-$Arg^9$ bradykinin (Regoli, D. and Barabe, J. (1980) Pharmacol. Rev. 32, 1-46). Structure-activity studies using residue 8 (Phe) substituted analogues indicated that antagonist activity increased with length of aliphatic side chain such that Ala <<cyclohexylalanine<Leu. Further modifications, such as amidation or esterification of the C-terminus of the leucyl residue, substitution by the branched-chained isoleucyl residue or the straight-chained, norleucyl residue, did not further increase affinity (Regoli, D. and Barabe, J. (1980) Pharmacol. Rev. 32, 1-46).

$Leu^8$-bradykinin, although chemically-synthesised for previous bradykinin structure/activity studies, has been found to occur in nature in various forms. Ornithokinin, the avian analogue of bradykinin, was generated in both chicken and pigeon plasma and its structure was established as ($Thr^6$, $Leu^8$)-bradykinin (Kimura M et al Eur. J. Biochem. 1987; 168:493-501). The autologous receptor was subsequently cloned from chicken and expressed (Schroeder et L, J. Biol. Chem. 1997; 272:12475-12481). Radioreceptor binding assays showed that the affinity for ornithokinin, using ($Tyr^0$)-radioiodinated ornithokinin as competing ligand, was some three to four orders of magnitude lower ($4.7 \times 10^{-9}$M vs >$1 \times 10^{-6}$M) than bradykinin. Also, Hoe 140, a potent mammalian $B_2$-receptor antagonist, functioned as a partial agonist at this recombinantly-expressed receptor (Lemback et al, Br. J. Pharmacol. 1991; 102: 297-304).

As described above, kinestatin is approximately x10 more potent as a bradykinin antagonist than $Leu^8$ bradykinin.

TABLE 1

Alignment of the primary structure of kinestatin with bradykinin and related nonapeptides from amphibian skin. The primary structures of ornithokinin and the bradykinin B2-receptor antagonist, HOE-140, are included for comparison. (references in parentheses)

Kinestatin
pGlu-Ile-Pro-Gly-Leu-Gly-Pro-Leu-Arg.NH$_2$
(SEQ ID NO: 3)

TABLE 1-continued

Alignment of the primary structure of kinestatin with bradykinin and related nonapeptides from amphibian skin. The primary structures of ornithokinin and the bradykinin B2-receptor antagonist, HOE-140, are included for comparison. (references in parentheses)

```
pGlu-Ile-Pro-Gly-Leu-Gly-Pro-Leu-Arg
(SEQ ID NO: 10)
Gln-Ile-Pro-Gly-Leu-Gly-Pro-Leu-Arg-NH2
(SEQ ID NO: 11)

Bradykinin
Arg-Pro-Pro-Gly-Phe-Ser-Pro-Phe-Arg[4,9]
(SEQ ID NO: 12)

(Thr-6)-bradykinin
Arg-Pro-Pro-Gly-Phe-Thr-Pro-Phe-Arg[5,9]
(SEQ ID NO: 13)

(Leu-8)-bradykinin
Arg-Pro-Pro-Gly-Phe-Ser-Pro-Leu-Arg[17]
(SEQ ID NO: 14)

(Val-1,Thr-6)-bradykinin
Val-Pro-Pro-Gly-Phe-Thr-Pro-Phe-Arg[5]
(SEQ ID NO: 15)

(Ala-3, Thr-6)-bradykinin
Arg-Pro-Ala-Gly-Phe-Thr-Pro-Phe-Arg[10]
(SEQ ID NO: 16)

(Val-1,Thr-3,Thr-6)-bradykinin
Val-Pro-Thr-Gly-Phe-Thr-Pro-Phe-Arg[10]
(SEQ ID NO: 17)

Ornithokinin
Arg-Pro-Pro-Gly-Phe-Thr-Pro-Leu-Arg[19]
(SEQ ID NO: 18)

HOE-140
Arg-Arg-Pro-Hyp-Gly-Thi-Ser-Tic-Oic-Arg[22]
(SEQ ID NO: 19)
Gln-Ile-Pro-Gly-Leu-Gly-Pro-Leu-Arg
(SEQ ID NO: 20)
``` conserved residues in natural peptides in bold type.
In HOE-140, underlined residues (Arg[1] and Tic[8]) are D-isomers.
Non-standard abbreviations: Hyp - hydroxyproline, Thi -β-(2-thienyl-)-L-alanine, Tic - tetrahydroisoquinoline-3-carboxylic acid, Oic - octahydroindole-2-carboxylic acid.
Table 1 References
[5]Yasuhara et al, R. Chem. Pharm. Bull. (Tokyo) 1979; 27:486-491.
[10]Chen T et al, Eur. J. Biochem. 2002; 269:4693-4700.
[19]Kimura et al, Eur. J. Biochem. 1987; 168:493-501.
[22]Duellman WE, Trueb L. Biology of Amphibians. Johns Hopkins University Press, Baltimore/London; 1994

Example 2

Analysis of the Anti-Angiogenic Effects of Kinestatin

The anti-angiogenic capability of kinestatin was compared throughout to non-treated controls and those treated with fumagillin, a widely-used anti-angiogenic therapeutic of fungal origin.

Figure 8:
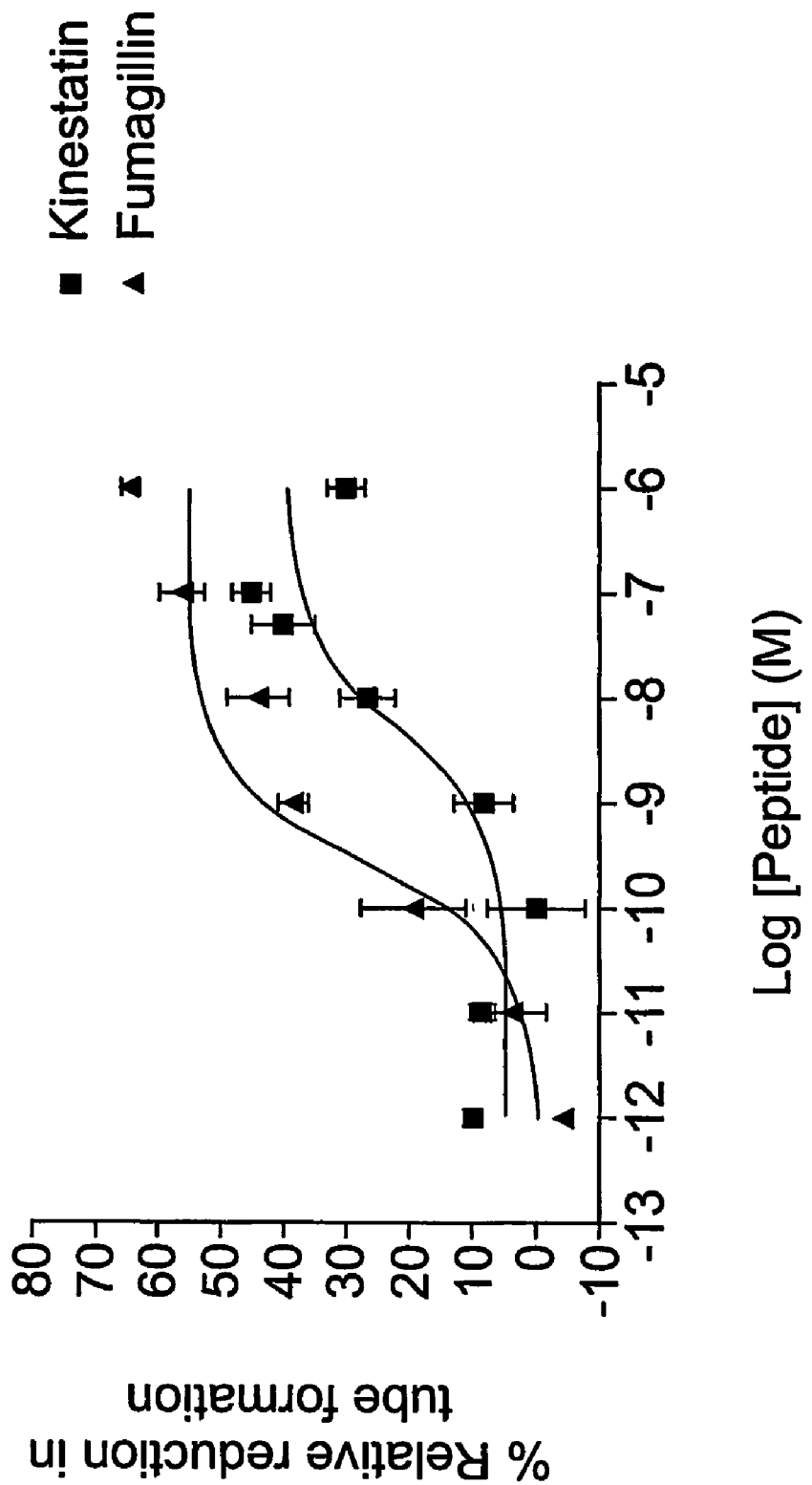
FIG. 8 is a graph comparing the ability of kinestatin (■) and fumagillin (▲) to inhibit the formation of endothelial tube structures on Matrigel matrix plates.

Expt. 1 clearly demonstrates an inhibitory effect on tube formation in a classical Matrigel assay that is comparable in magnitude to that observed with fumagillin (FIG. 8)

Figure 9:
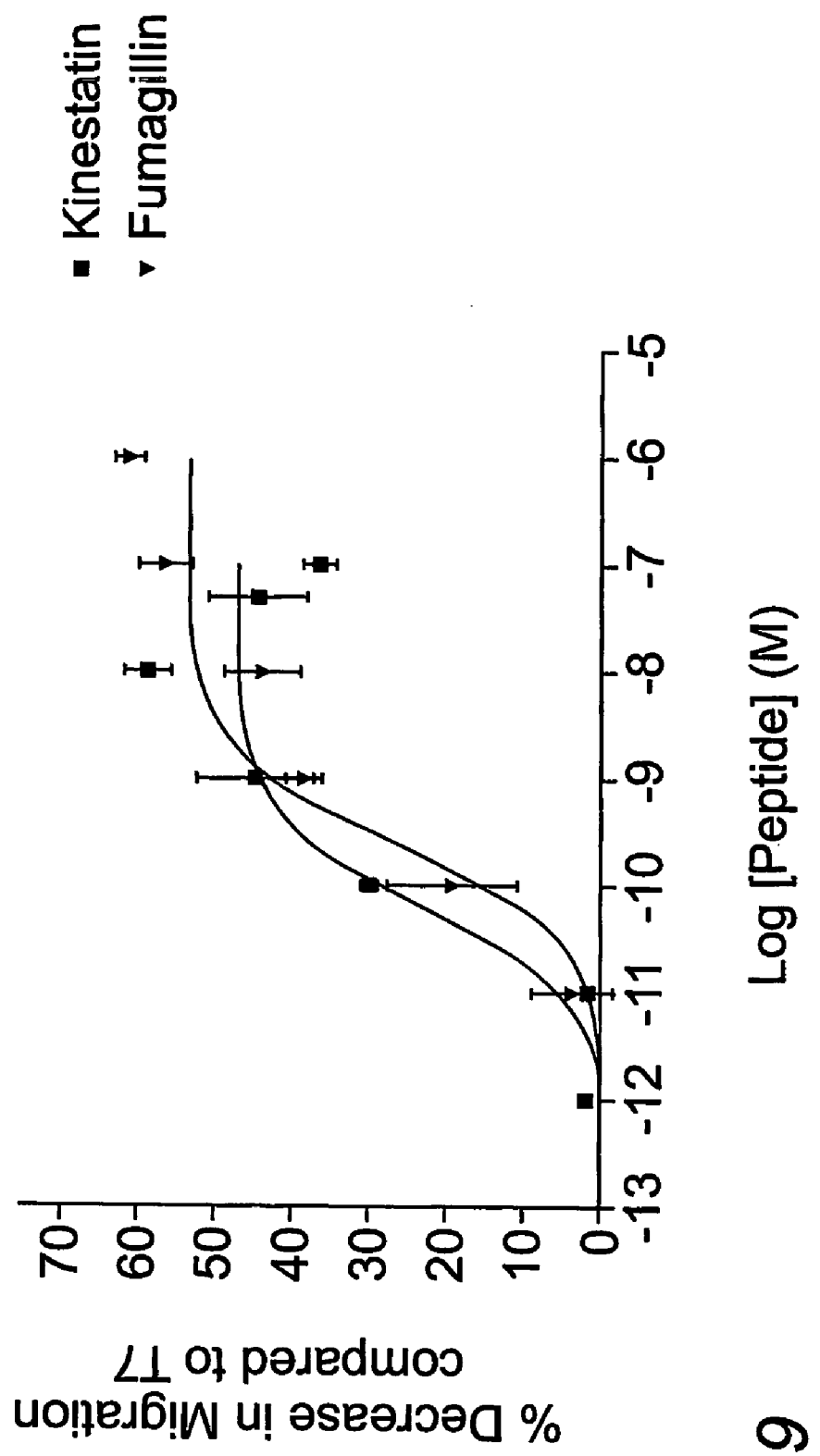
FIG. 9 is a graph comparing the ability of kinestatin (■) and fumagillin (▼) to inhibit the migration of human microvascular endothelial cells (HMEC-1) into a wound in a dose- and time-dependent manner
Figure 10:
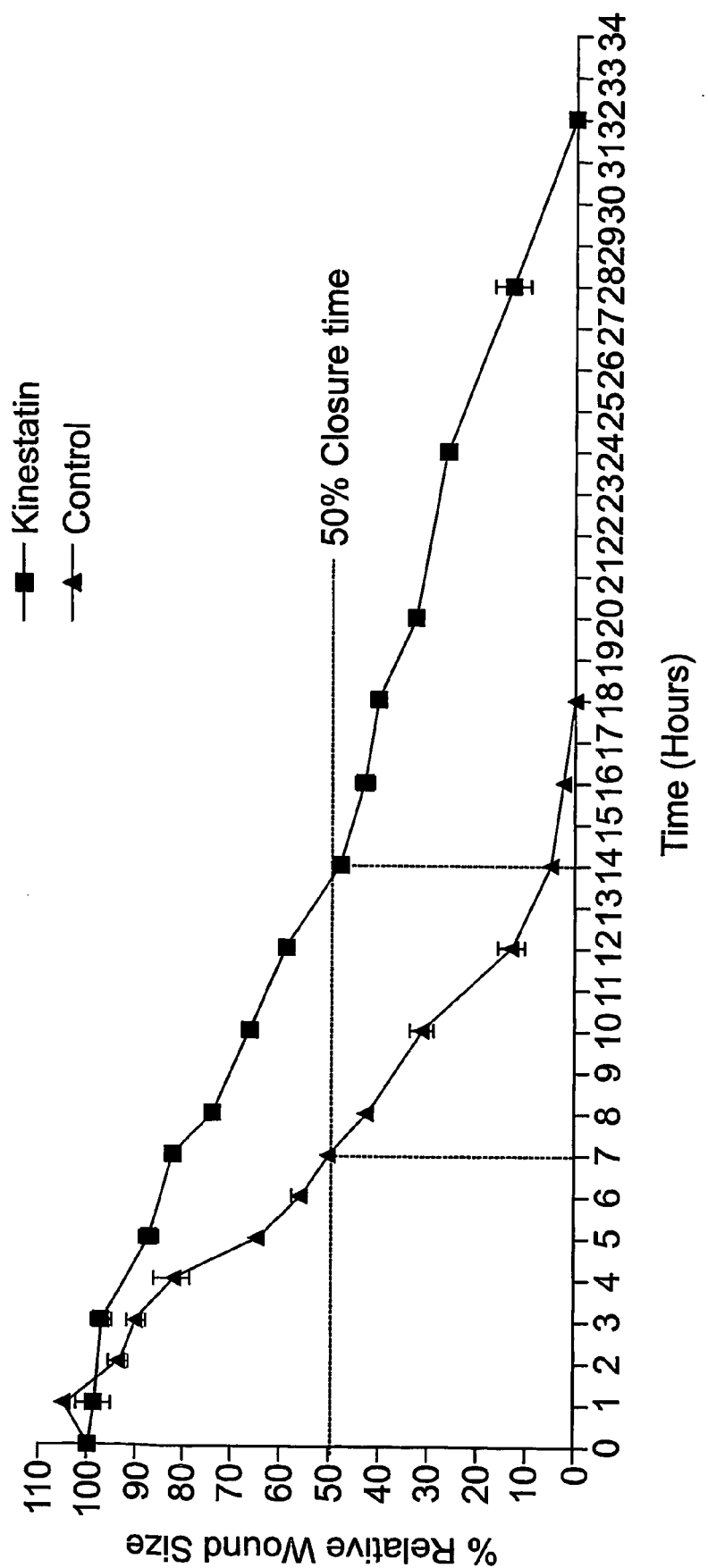
FIG. 10 is a time response curve showing the delay in complete closure of endothelial cell 1 cm wounds in the presence of kinestatin (■) and non-treated control cells (▲).

Expt. 2 demonstrates an inhibition in endothelial cell migration as judged by the time required to effect half closure of a 1 cm wide wound induced in a cell monolayer. The same maximal inhibitory effect was observed with both kinestatin and fumagillin although kinestatin was more potent on a molar basis (FIG. 9). Kinestatin prolonged wound closure time by 100% from 7 h (control) to 14 h (treatment) (FIG. 10).

Figure 11:
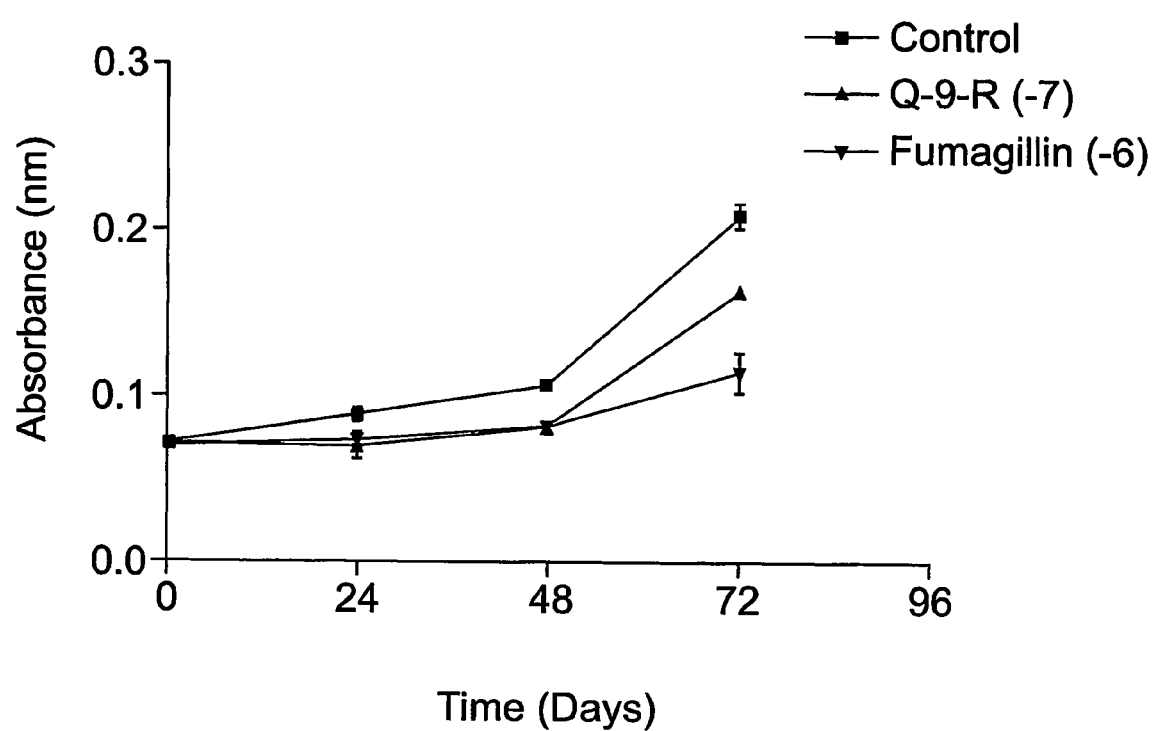
FIG. 11 is a graph comparing the effect of control (■), kinestsin (Q-9-R-(-7) (▲) and fumagillin (▼) on the proliferation of the human microvascular endothelial cell line (HMEC-1).
Figure 12:
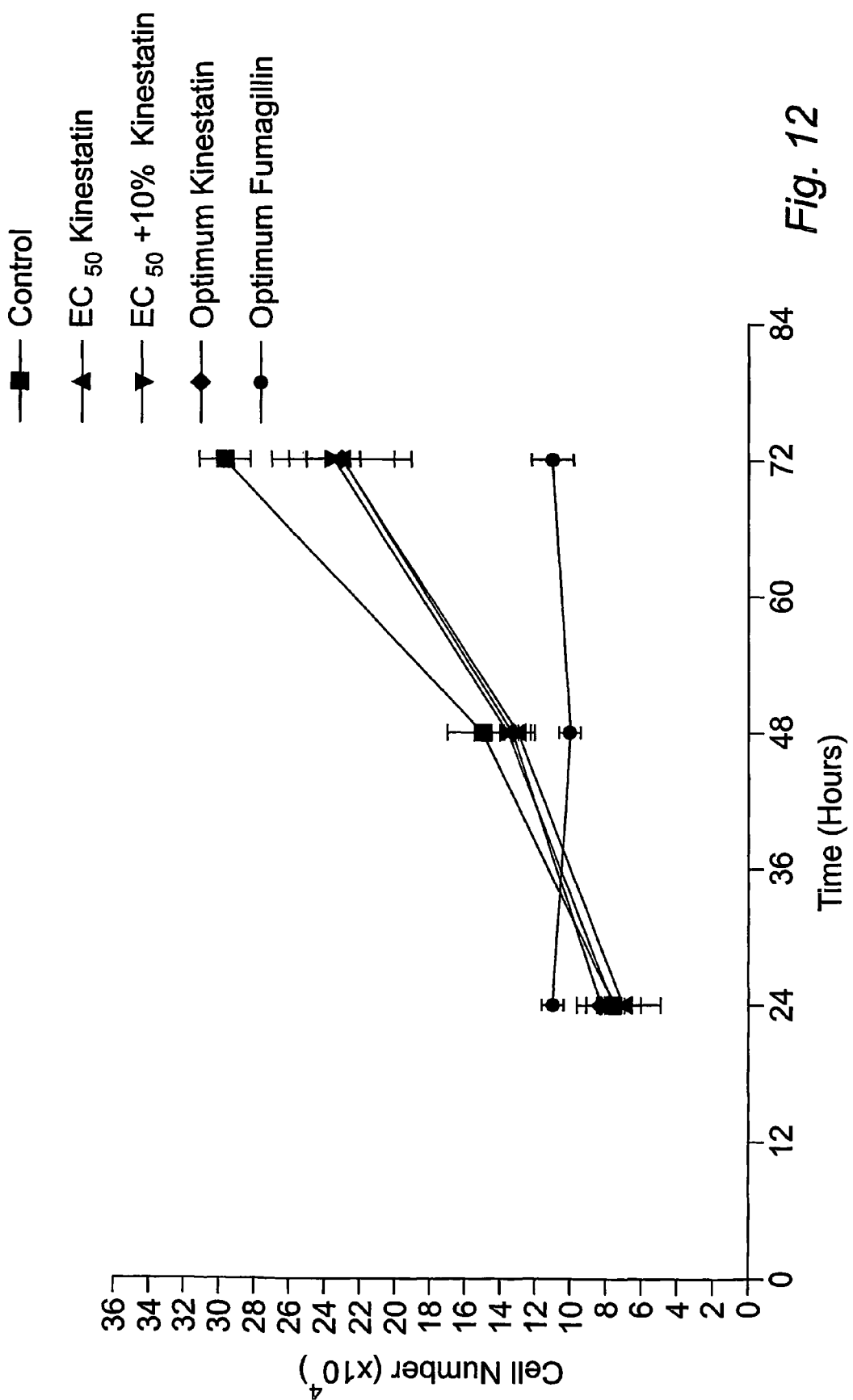
FIG. 12 is a graph comparing the effect of kinestatin and fumagillin on the proliferation of the adenocarcinoma cell line HT29, in terms of cell numbers (X $10^4$) over time (hours). Results for the control are shown as (■), the $EC_{50}$ of kinestatin is shown as (▲), the $EC_{50}$ plus 10% kinestatin is shown as (▼), the optimum kinestatin concentration is shown as (♦), and the optimum fumagillin concentration is shown as (●).

Expt. 3 demonstrated that both kinestatin and fumagillin had profound effects on inhibition of cell proliferation (FIG. 11), an effect that was also demonstrable on an epithelial adeno-) carcinoma cell line (HT29) (FIG. 12).

Imaging of kinestatin-treated endothelial cells revealed significant changes in cellular microarchitecture. The orientation of cytoskeletal structures was most evident when control cells were compared with kinestatin-treated cells and viewed following immunochemical demonstration of components by confocal laser imaging. Microtubule orientation was entirely disrupted resulting in an infranuclear deposition rather than alignment to facilitate migration. Dynein was likewise localized as a nuclear halo with no netwoks detected in treated cells. Intermediate filaments displayed no directional orientation.

These cellular observations are consistent with the data derived from experiments 1 through 3 of this example, in which migration and angiogenic tube formation were inhibited implicitly through disorganization of facilitatory cytoskeletal components.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

---

The invention claimed is:

1. An isolated peptide having bradykinin antagonist activity, wherein said peptide comprises the amino acid sequence:
Xaa-Ile-Pro-Gly-Leu-Gly-Pro-Leu-Arg (SEQ ID NO: 23), wherein Xaa is Glu or p-Glu, where p-Glu is pyroglutamate, and the C-terminal amino acid is optionally amidated.

2. The peptide according to claim 1, wherein said peptide comprises the amino acid sequence: pGlu-Ile-Pro-Gly-Leu-Gly-Pro-Leu-Arg-NH$_2$ (SEQ ID NO: 3), where Arg-NH$_2$ is Arg-amide.

3. The peptide according to claim 1, wherein the peptide is a nonapeptide.

4. The peptide according to claim 1, wherein said peptide has selective bradykinin B$_2$ receptor antagonist activity.

5. A multimeric peptide comprising the peptide of claim 1.

6. A peptide prodrug comprising the peptide according to claim 1, wherein said peptide prodrug either has bradykinin antagonist activity or is capable of having bradykinin antagonist activity when the peptide is released following administration.

7. The prodrug of claim 6, wherein the prodrug is a peptide-polymer conjugate, wherein the polymer comprises a polyalkylene glycol moiety.

8. The prodrug of claim 7, wherein the polyalkylene glycol moiety is a polyethylene glycol moiety.

9. A pharmaceutical composition comprising the peptide according to claim 1, and a pharmaceutically acceptable carrier or excipient.

10. The peptide according to claim 1, wherein Xaa is pGlu.

11. The peptide according to claim 1, wherein the C-terminal peptide is amidated.

12. The peptide according to claim 1 consisting of the amino acid sequence: pGlu-Ile-Pro-Gly-Leu-Gly-Pro-Leu-Arg-NH$_2$ (SEQ ID NO: 3), where Arg-NH$_2$ is Arg-amide.

13. A method of antagonising bradykinin activity in a cell, tissue or organism, said method comprising administering an effective amount of a peptide according to claim 1 to said cell, tissue or organism to antagonise bradykinin activity.

14. The method according to claim 13, wherein said bradykinin activity is mediated via bradykinin B$_2$ receptors.

15. The method according to claim 13, wherein the peptide is administered as a peptide prodrug.

16. A method of constricting vascular smooth muscle, said method comprising administering a peptide according to claim 1 to said smooth muscle.

17. A method of treating a condition associated with bradykinin activity, said method comprising administering a therapeutically effective amount of a peptide according to claim 1 to a patient in need thereof to treat said condition associated with bradykinin activity.

18. The method according to claim 17, wherein the condition is selected from the group consisting of inflammation and inflammatory disorders, cardiovascular diseases, pain, common cold, allergies and immunology/allergy disorders, asthma, pancreatitis, burns and other skin disorders, infectious diseases, head injury, and multiple trauma.

19. The method according to claim 17, wherein the condition is selected from the group consisting of respiratory diseases, diuresis, natriuresis, calciuresis, COPD (chronic obstructive pulmonary disease), liver/kidney diseases, metabolic disorders, metastasis, neovascularization, eye disorders, and angio edema.

20. The method according to claim 17, wherein the condition is selected from the group consisting of Alzheimer's disease, Huntington's disease, Parkinson's disease, amyotrophic lateral sclerosis, multiple sclerosis, stroke, head trauma, post-surgical brain edema, brain edema (general), cytotoxic brain edema, migraine, neuropathic pain, pruritis, brain tumors and other cancers, pseudotumor cerebri, glaucoma, hydrocephalus, spinal cord trauma, spinal cord edema, neurodegenerative diseases, and post-traumatic brain injury.

21. The method according to claim 17 wherein said condition is a cardiovascular condition, a neurological condition or a degenerative condition.

22. The method according to claim 21 wherein the degenerative condition is Alzheimer's disease.

23. The method according to claim 17, wherein said bradykinin activity is mediated via bradykinin B$_2$ receptors.

24. A method of inhibiting angiogenesis, comprising administering to a patient in need of treatment thereof an effective, angiogenesis inhibiting amount of a peptide according to claim 1.

25. The method of claim 24, wherein said peptide is present in or conjugated onto a liposome or microparticle that is of a suitable size for intraveneous administration but that lodges in capillary beds.

26. The method of claim 25, further comprising administering a COX-2 inhibitor.

27. The method of claim 24, wherein the method is used to treat one or more tumors, autoimmune disorders, hereditary disorders, or ocular disorders.

28. The method of claim 27, wherein the disorders are selected from the group consisting of hemangioma, solid tumors, leukemia, metastasis, telangiectasia, psoriasis, scleroderma, pyogenic granuloma, myocardial angiogenesis, Crohn's disease, plaque neovascularization, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, Helicobacter related diseases, fractures, keloids, and vasculogenesis.

29. The method of claim 27, wherein the tumors are selected from the group consisting of colorectal carcinoma, gastric carcinoma, signet ring type, esophageal carcinoma, intestinal type, mucinous type, pancreatic carcinoma, lung carcinoma, breast carcinoma, renal carcinoma, bladder carcinoma, prostate carcinoma, testicular carcinoma, ovarian carcinoma, endometrial carcinoma, thyroid carcinoma, liver carcinoma, larynx carcinoma, mesothelioma, neuroendocrine carcinomas, neuroectodermal tumors, melanoma, gliomas, neuroblastomas, sarcomas, leiomyosarcoma, MFII, fibrosarcoma, liposarcoma, MPNT, chondrosarcoma, and lymphomas.

30. The method of claim 27, wherein the ocular disorders are selected from the group consisting of ocular neovascular disease, age-related macular degeneration, diabetic retinopathy, retinopathy of prematurity, corneal graft rejection, neovascular glaucoma, retrolental fibroplasias, epidemic keratoconjunctivitis, Vitamin A deficiency, atopic keratitis, superior limbic keratitis, pterygium keratitis sicca, periphigoid radial keratotomy, corneal graph rejection, macular degeneration, presumed myopia, optic pits, chronic retinal detachment, hyperviscosity syndromes, trauma to the eye, post-laser complications, rubeosis (neovascularization of the angle) and diseases caused by the abnormal proliferation of fibrovascular or fibrous tissue.

31. The method of claim 27, wherein the inflammatory disorder is selected from the group consisting of arthritis, ulcerative colitis, Crohn's disease, bartonellosis, and atherosclerosis.

* * * * *

SEQUENCE LISTING

```
<160> NUMBER OF SEQ ID NOS: 24

<210> SEQ ID NO 1
<211> LENGTH: 9
<212> TYPE: PRT
<213> ORGANISM: Artificial
<220> FEATURE:
<223> OTHER INFORMATION: Chemical synthesis
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (2)..(2)
```

```
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid

<400> SEQUENCE: 1

Xaa Xaa Xaa Gly Leu Xaa Pro Xaa Xaa
1               5

<210> SEQ ID NO 2
<211> LENGTH: 9
<212> TYPE: PRT
<213> ORGANISM: Artificial
<220> FEATURE:
<223> OTHER INFORMATION: Chemical synthesis
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid

<400> SEQUENCE: 2

Xaa Xaa Pro Xaa Leu Gly Xaa Xaa Xaa
1               5

<210> SEQ ID NO 3
<211> LENGTH: 9
<212> TYPE: PRT
<213> ORGANISM: Bombina maxima
<220> FEATURE:
<221> NAME/KEY: MISC_FEATURE
<222> LOCATION: (1)..(1)
<223> OTHER INFORMATION: Xaa is pyroglutamyl
<220> FEATURE:
<221> NAME/KEY: MOD_RES
<222> LOCATION: (9)..(9)
<223> OTHER INFORMATION: AMIDATION

<400> SEQUENCE: 3

Xaa Ile Pro Gly Leu Gly Pro Leu Arg
1               5
```

```
<210> SEQ ID NO 4
<211> LENGTH: 9
<212> TYPE: PRT
<213> ORGANISM: Artificial
<220> FEATURE:
<223> OTHER INFORMATION: Chemical synthesis
<220> FEATURE:
<221> NAME/KEY: MISC_FEATURE
<222> LOCATION: (9)..(9)
<223> OTHER INFORMATION: pyrogltutamyl
<220> FEATURE:
<221> NAME/KEY: MOD_RES
<222> LOCATION: (9)..(9)
<223> OTHER INFORMATION: AMIDATION

<400> SEQUENCE: 4

Arg Leu Pro Gly Leu Gly Pro Ile Xaa
1               5

<210> SEQ ID NO 5
<211> LENGTH: 27
<212> TYPE: DNA
<213> ORGANISM: Artificial
<220> FEATURE:
<223> OTHER INFORMATION: Chemical synthesis

<400> SEQUENCE: 5
caaattcctg gtttaggccc tctgcgt                                          27

<210> SEQ ID NO 6
<211> LENGTH: 548
<212> TYPE: DNA
<213> ORGANISM: Artificial
<220> FEATURE:
<223> OTHER INFORMATION: Chemical synthesis

<400> SEQUENCE: 6
tagttctcag tgtcacttcc agctctgatc atgagactgt ggttctgtct aagttttttc       60
atcgtcctgt gcctggagca ttttccagga accctggcag atgaaaggaa taatcgtgac      120
tacaccatca gaacccgctt acatggccat cataaaccaa gcaggaataa ccgttacgcc      180
atcaaaacca gcatacatgg ccatcatata ccaaggaatg ttccagagag tgaagaaaaa      240
actgagcagc tcctgaggga tttgcctaag atcaaccgca aaggaccacg tccaccgggg      300
ttctcccctt ttcgaggaaa attccatagc cagtccctac gacaaattcc tggtttaggc      360
cctctgcgtg gataacgaag ctcagggata agaatctgcc ctatgtgtat gccatgttca      420
ccataggcta aaaagtagcg tcccctgcta taaataagca ttgttatgtc acctctgtaa      480
taccagctct gactgacatg gtttattaaa cagcagattt gtgctctcta aaaaaaaaa      540 aaaaaaaa                                                              548

<210> SEQ ID NO 7
<211> LENGTH: 114
<212> TYPE: PRT
<213> ORGANISM: Artificial
<220> FEATURE:
<223> OTHER INFORMATION: Chemical synthesis

<400> SEQUENCE: 7

Met Arg Leu Trp Phe Cys Leu Ser Phe Phe Ile Val Leu Cys Leu Glu
1               5                   10                  15

His Phe Pro Gly Thr Leu Ala Asp Glu Arg Asn Asn Arg Asp Tyr Thr
            20                  25                  30

Ile Arg Thr Arg Leu His Gly His His Lys Pro Ser Arg Asn Asn Arg
        35                  40                  45
```

-continued

```
Tyr Ala Ile Lys Thr Ser Ile His Gly His His Ile Pro Arg Asn Val
        50                  55                  60
Pro Glu Ser Glu Glu Lys Thr Glu Gln Leu Leu Arg Asp Leu Pro Lys
 65                  70                  75                  80
Ile Asn Arg Lys Gly Pro Arg Pro Pro Gly Phe Ser Pro Phe Arg Gly
                 85                  90                  95
Lys Phe His Ser Gln Ser Leu Arg Gln Ile Pro Gly Leu Gly Pro Leu
                100                 105                 110
Arg Gly

<210> SEQ ID NO 8
<211> LENGTH: 22
<212> TYPE: DNA
<213> ORGANISM: Artificial
<220> FEATURE:
<223> OTHER INFORMATION: Chemical synthesis

<400> SEQUENCE: 8
agttctcagt gtcacttcca gc                                              22

<210> SEQ ID NO 9
<211> LENGTH: 9
<212> TYPE: PRT
<213> ORGANISM: Artificial
<220> FEATURE:
<223> OTHER INFORMATION: Chemical synthesis
<220> FEATURE:
<221> NAME/KEY: MISC_FEATURE
<222> LOCATION: (1)..(1)
<223> OTHER INFORMATION: Xaa is pyroglutamyl
<220> FEATURE:
<221> NAME/KEY: MISC_FEATURE
<222> LOCATION: (2)..(2)
<223> OTHER INFORMATION: Xaa can be Leu or Ile
<220> FEATURE:
<221> NAME/KEY: MISC_FEATURE
<222> LOCATION: (5)..(5)
<223> OTHER INFORMATION: Xaa can be Leu or Ile
<220> FEATURE:
<221> NAME/KEY: MISC_FEATURE
<222> LOCATION: (8)..(8)
<223> OTHER INFORMATION: Xaa can be Leu or Ile
<220> FEATURE:
<221> NAME/KEY: MOD_RES
<222> LOCATION: (9)..(9)
<223> OTHER INFORMATION: AMIDATION

<400> SEQUENCE: 9

Xaa Xaa Pro Gly Xaa Gly Pro Xaa Arg
 1               5

<210> SEQ ID NO 10
<211> LENGTH: 9
<212> TYPE: PRT
<213> ORGANISM: Artificial
<220> FEATURE:
<223> OTHER INFORMATION: Chemical synthesis
<220> FEATURE:
<221> NAME/KEY: MISC_FEATURE
<222> LOCATION: (1)..(1)
<223> OTHER INFORMATION: Xaa is pyroglutamyl

<400> SEQUENCE: 10

Xaa Ile Pro Gly Leu Gly Pro Leu Arg
 1               5

<210> SEQ ID NO 11
<211> LENGTH: 9
```

```
<212> TYPE: PRT
<213> ORGANISM: Artificial
<220> FEATURE:
<223> OTHER INFORMATION: Chemical synthesis
<220> FEATURE:
<221> NAME/KEY: MOD_RES
<222> LOCATION: (9)..(9)
<223> OTHER INFORMATION: AMIDATION

<400> SEQUENCE: 11

Gln Ile Pro Gly Leu Gly Pro Leu Arg
1               5

<210> SEQ ID NO 12
<211> LENGTH: 9
<212> TYPE: PRT
<213> ORGANISM: Rana palustris

<400> SEQUENCE: 12

Arg Pro Pro Gly Phe Ser Pro Phe Arg
1               5

<210> SEQ ID NO 13
<211> LENGTH: 9
<212> TYPE: PRT
<213> ORGANISM: Rana rugosa

<400> SEQUENCE: 13

Arg Pro Pro Gly Phe Thr Pro Phe Arg
1               5

<210> SEQ ID NO 14
<211> LENGTH: 9
<212> TYPE: PRT
<213> ORGANISM: Rana palustris

<400> SEQUENCE: 14

Arg Pro Pro Gly Phe Ser Pro Leu Arg
1               5

<210> SEQ ID NO 15
<211> LENGTH: 9
<212> TYPE: PRT
<213> ORGANISM: Rana Nigromaculata

<400> SEQUENCE: 15

Val Pro Pro Gly Phe Thr Pro Phe Arg
1               5

<210> SEQ ID NO 16
<211> LENGTH: 9
<212> TYPE: PRT
<213> ORGANISM: Bombina variegata

<400> SEQUENCE: 16

Arg Pro Ala Gly Phe Thr Pro Phe Arg
1               5

<210> SEQ ID NO 17
<211> LENGTH: 9
<212> TYPE: PRT
<213> ORGANISM: Bombina variegata

<400> SEQUENCE: 17

Val Pro Thr Gly Phe Thr Pro Phe Arg
1               5
```

```
<210> SEQ ID NO 18
<211> LENGTH: 9
<212> TYPE: PRT
<213> ORGANISM: Gallus gallus

<400> SEQUENCE: 18

Arg Pro Pro Gly Phe Thr Pro Leu Arg
1               5

<210> SEQ ID NO 19
<211> LENGTH: 10
<212> TYPE: PRT
<213> ORGANISM: Artificial
<220> FEATURE:
<223> OTHER INFORMATION: Chemical synthesis
<220> FEATURE:
<221> NAME/KEY: MISC_FEATURE
<222> LOCATION: (1)..(1)
<223> OTHER INFORMATION: Xaa is Arg
<220> FEATURE:
<221> NAME/KEY: MISC_FEATURE
<222> LOCATION: (1)..(1)
<223> OTHER INFORMATION: Xaa is D-isomer amino acid
<220> FEATURE:
<221> NAME/KEY: MISC_FEATURE
<222> LOCATION: (4)..(4)
<223> OTHER INFORMATION: Xaa is hydroxyproline
<220> FEATURE:
<221> NAME/KEY: MISC_FEATURE
<222> LOCATION: (6)..(6)
<223> OTHER INFORMATION: Xaa is beta-(2-thienyl)-L-alanine
<220> FEATURE:
<221> NAME/KEY: MISC_FEATURE
<222> LOCATION: (8)..(8)
<223> OTHER INFORMATION: Xaa is tetrahydroisoquinoline-3-carboxylic acid
      D-isomer
<220> FEATURE:
<221> NAME/KEY: MISC_FEATURE
<222> LOCATION: (9)..(9)
<223> OTHER INFORMATION: Xaa is octahydroindole-2-carboxylic acid

<400> SEQUENCE: 19

Xaa Arg Pro Xaa Gly Xaa Ser Xaa Xaa Arg
1               5                   10

<210> SEQ ID NO 20
<211> LENGTH: 9
<212> TYPE: PRT
<213> ORGANISM: Artificial
<220> FEATURE:
<223> OTHER INFORMATION: Chemical synthesis

<400> SEQUENCE: 20

Gln Ile Pro Gly Leu Gly Pro Leu Arg
1               5

<210> SEQ ID NO 21
<211> LENGTH: 9
<212> TYPE: PRT
<213> ORGANISM: Artificial
<220> FEATURE:
<223> OTHER INFORMATION: chemical synthesis
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (3)..(3)
```

```
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid

<400> SEQUENCE: 21

Xaa Xaa Xaa Gly Leu Xaa Pro Xaa Arg

<210> SEQ ID NO 22
<211> LENGTH: 9
<212> TYPE: PRT
<213> ORGANISM: Artificial
<220> FEATURE:
<223> OTHER INFORMATION: chemical synthesis
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid

<400> SEQUENCE: 22

Arg Xaa Pro Xaa Leu Gly Xaa Xaa Xaa
1               5

<210> SEQ ID NO 23
<211> LENGTH: 9
<212> TYPE: PRT
<213> ORGANISM: Artificial
<220> FEATURE:
<223> OTHER INFORMATION: chemical synthesis
<220> FEATURE:
<221> NAME/KEY: MISC_FEATURE
<222> LOCATION: (1)..(1)
<223> OTHER INFORMATION: Xaa can be Gln or pyroglutamyl)
<220> FEATURE:
<221> NAME/KEY: MISC_FEATURE
<222> LOCATION: (9)..(9)
<223> OTHER INFORMATION: AMIDATION or not AMIDATION

<400> SEQUENCE: 23

Xaa Ile Pro Gly Leu Gly Pro Leu Arg

<210> SEQ ID NO 24
<211> LENGTH: 9
<212> TYPE: PRT
<213> ORGANISM: Artificial
<220> FEATURE:
<223> OTHER INFORMATION: chemical synthesis
<220> FEATURE:
<221> NAME/KEY: MISC_FEATURE
<222> LOCATION: (9)..(9)
<223> OTHER INFORMATION: Xaa can be Gln or pyroglutamyl)
<220> FEATURE:
<221> NAME/KEY: MISC_FEATURE
```

```
<222> LOCATION: (9)..(9)
<223> OTHER INFORMATION: AMIDATION or not AMIDATION

<400> SEQUENCE: 24

Arg Leu Pro Gly Leu Gly Pro Ile Xaa
```